(12) United States Patent
Ibay et al.

(10) Patent No.: US 12,378,380 B2
(45) Date of Patent: Aug. 5, 2025

(54) BROMINATED FLAME RETARDANTS AND POLYURETHANES CONTAINING THE SAME

(71) Applicant: ALBEMARLE CORPORATION, Charlotte, NC (US)

(72) Inventors: Augusto C. Ibay, Baton Rouge, LA (US); Tse-Chong Wu, Baton Rouge, LA (US); Charles D. Varnado, Jr., Denham Springs, LA (US); Yunqi Liu, Baton Rouge, LA (US)

(*) Notice: Subject to any disclaimer, the term of this patent is extended or adjusted under 35 U.S.C. 154(b) by 989 days.

(21) Appl. No.: 17/418,307

(22) PCT Filed: Dec. 20, 2019

(86) PCT No.: PCT/US2019/067750
§ 371 (c)(1),
(2) Date: Jun. 25, 2021

(87) PCT Pub. No.: WO2020/139742
PCT Pub. Date: Jul. 2, 2020

(65) Prior Publication Data
US 2021/0388169 A1    Dec. 16, 2021

Related U.S. Application Data

(60) Provisional application No. 62/785,483, filed on Dec. 27, 2018.

(51) Int. Cl.
| | | |
|---|---|---|
| *C07C 17/04* | (2006.01) | |
| *C07C 17/25* | (2006.01) | |
| *C07C 19/075* | (2006.01) | |
| *C07C 21/14* | (2006.01) | |
| *C07C 29/124* | (2006.01) | |
| *C07C 29/14* | (2006.01) | |
| *C07C 29/62* | (2006.01) | |
| *C07C 33/42* | (2006.01) | |
| *C07C 41/16* | (2006.01) | |
| *C07C 41/22* | (2006.01) | |
| *C08G 18/38* | (2006.01) | |
| *C08G 18/40* | (2006.01) | |
| *C08G 18/42* | (2006.01) | |
| *C08G 18/48* | (2006.01) | |
| *C08G 18/66* | (2006.01) | |
| *C08G 18/67* | (2006.01) | |
| *C08G 18/76* | (2006.01) | |
| *C08J 9/12* | (2006.01) | |
| *C08J 9/14* | (2006.01) | |

(52) U.S. Cl.
CPC .......... *C08J 9/127* (2013.01); *C08G 18/4018* (2013.01); *C08G 18/4208* (2013.01); *C08G 18/4829* (2013.01); *C08G 18/485* (2013.01); *C08G 18/4883* (2013.01); *C08G 18/6775* (2013.01); *C08G 18/7671* (2013.01); *C08J 9/125* (2013.01); *C08J 9/146* (2013.01); *C08J 2203/10* (2013.01); *C08J 2203/162* (2013.01); *C08J 2203/182* (2013.01); *C08J 2375/12* (2013.01)

(58) Field of Classification Search
CPC ... C07C 19/075; C07C 21/14; C08G 18/3068; C08G 18/381; C08G 18/6775
See application file for complete search history.

(56) References Cited

U.S. PATENT DOCUMENTS

| | | |
|---|---|---|
| 3,267,070 A | 8/1966 | Tousignant et al. |
| 3,283,013 A | 11/1966 | Rimmer et al. |
| 3,284,515 A | 11/1966 | Dickerson et al. |
| 3,334,032 A | 8/1967 | Kardos |
| 3,487,040 A | 12/1969 | Jolles |
| 3,542,740 A | 11/1970 | Pumpelly et al. |
| 3,637,813 A | 1/1972 | D'Alelio |
| 3,764,546 A | 10/1973 | Feltzin et al. |
| 3,780,144 A | 12/1973 | D'Alelio |
| 3,932,181 A | 1/1976 | Ray-Chaudhuri et al. |
| 3,933,690 A | 1/1976 | D'Alelio et al. |

(Continued)

FOREIGN PATENT DOCUMENTS

| | | |
|---|---|---|
| CA | 2182714 A1 | 2/1997 |
| CN | 101092535 A | 12/2007 |

(Continued)

OTHER PUBLICATIONS

A.W. Johnson, 2-Butyne-1 : 4-diol. Part II. Reactions involving the Triple Bond, Journal of the Chemical Society (Resumed), 1946, pp. 1014-1017.

Ewis F. Hatch, et al., Dehydrohalogenation of Several Vinyl Halides, Dec. 2, 1949, pp. 654-658, Department of Chemistry, the University of Texas, Austin, Texas.

J. Cousseau, A New Route to 2-Bromo-1-alkenes by Hydrobromination of 1-Alkynes with Tetraethylammonium Hydrogen Dibromide, Synthesis Communications, Oct. 1980, pp. 805-806, Georg Thieme Verlag Stuttgart, New York.

(Continued)

*Primary Examiner* — Melissa A Rioja

(57) ABSTRACT

The disclosure includes brominated alkenyl alcohols, their use as a flame retardant in polyurethane and polyurethane foams, and polyurethanes containing the brominated alkenyl alcohols. Compositions, methods, and processes are disclosed. The brominated alkenyl alcohols used as flame retardants in polyurethanes can be generally described by Formula (I), the scope of which is disclosed herein.

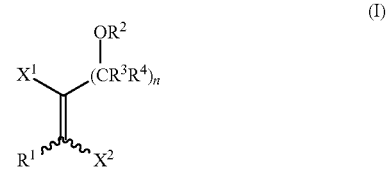

18 Claims, 2 Drawing Sheets

(56) References Cited

U.S. PATENT DOCUMENTS

| | | | |
|---|---|---|---|
| 3,950,392 | A | 4/1976 | D'Alelio |
| 3,993,690 | A | 11/1976 | Suvorov et al. |
| 4,002,580 | A | 1/1977 | Russo |
| 4,022,718 | A | 5/1977 | Russo |
| 4,559,366 | A | 12/1985 | Hostettler |
| 4,697,029 | A | 9/1987 | Collin et al. |
| 4,725,628 | A * | 2/1988 | Garvey ................ C08G 18/675 521/905 |
| 4,745,133 | A | 5/1988 | Grinbergs et al. |
| 4,898,981 | A | 2/1990 | Falk et al. |
| 7,671,105 | B2 | 3/2010 | Krupa et al. |
| 7,862,749 | B2 | 1/2011 | Sjerps |
| 9,434,884 | B2 | 9/2016 | Lubnin et al. |
| 2002/0107422 | A1 | 8/2002 | Doi et al. |
| 2003/0092786 | A1 | 5/2003 | Brassat et al. |
| 2003/0153656 | A1 | 8/2003 | Sjerps |
| 2006/0135636 | A1 | 6/2006 | Zhu et al. |
| 2008/0203348 | A1 | 8/2008 | Laoutid et al. |
| 2009/0186543 | A1 | 7/2009 | Keshavaraj et al. |
| 2013/0217286 | A1 | 8/2013 | Lubnin et al. |
| 2014/0005288 | A1 | 1/2014 | Chen et al. |
| 2014/0171525 | A1 | 6/2014 | Yu et al. |
| 2014/0220333 | A1 | 8/2014 | Bogdan et al. |
| 2015/0025164 | A1 | 1/2015 | Golini et al. |
| 2016/0251491 | A1 | 9/2016 | Okada et al. |
| 2017/0247496 | A1 | 8/2017 | Wang et al. |
| 2019/0202972 | A1 | 7/2019 | Wu et al. |
| 2020/0140601 | A1 | 5/2020 | Tang et al. |
| 2020/0140639 | A1 | 5/2020 | Wu et al. |

FOREIGN PATENT DOCUMENTS

| | | |
|---|---|---|
| CN | 102964562 A | 3/2013 |
| CN | 103102844 A | 5/2013 |
| CN | 103665915 A | 3/2014 |
| CN | 105860505 A | 8/2016 |
| CN | 106280451 A | 1/2017 |
| CN | 106317873 A | 1/2017 |
| CN | 106380600 A | 2/2017 |
| DE | 2344254 A | 3/1974 |
| EP | 0757068 A1 | 2/1997 |
| EP | 1756224 A1 | 2/2007 |
| FR | 1502050 A | 11/1967 |
| GB | 2019858 A | 11/1979 |
| IN | 105837781 A | 8/2016 |
| JP | H09039104 A | 2/1997 |
| WO | 2019005837 A1 | 1/2017 |
| WO | 2019067047 A1 | 4/2019 |

OTHER PUBLICATIONS

Mitsuo Kodomari, et al., Stereoselective Bromination of Acetylenes with Bromine in the Presence of Graphite, Bull, Chem. Soc. Jpn., 1989, pp. 4053-4054, vol. 62, No. 12, Tokyo, Japan.

Jon Efskind, et al., Stereoselective Synthesis of Alkenyl a,a'-Bridged Bis(glycines) using Palladium Promoted Substitution in the Bridge, Acta Chemica Scandinavica, 1997, pp. 942-952, vol. 51, Oslo, Norway.

George A. Kraus, et al., An Improved Synthesis of 3-Substituted Furans From Substituted Butene-1, 4-diols, Synthetic Communications, 1998, pp. 1093-1096, vol. 28, Issue 6, Marcel Dekker, Inc.

David Rennison, et al., Synthesis and Activity Studies of Analogues of the Rat Selective Toxicant Norbormide, Bioorganic & Medicinal Chemistry, 2007, pp. 2963-2974, vol. 15, Elsevier Ltd.

Kerstin Schuh, et al., A Domino Copper-Catalyzed C—N and C—O Cross-Coupline for the Conversion of Primary Amides into Oxazoles, Synthesis, 2007, pp. 2297-2306, No. 15, Georg Thieme Verlag Sutttgart, New York.

H.A. Gharibyan, et al., Hydroalumination-Bromination of Acetylenic a-Alcohols, Hayastani Kimiakan Handes, 2009, vol. 62, pp. 369-377.

ICL Products, Fire Safety in Construction and Building with ICL-IP Solutions, Brochure, pp. 1-6.

Sanket Bhoyate, et al., Highly Flame-Retardant Bio-Based Polyurethanes Using Novel Reactive Polyols, Journal of Applied Polymer Science, 2017, pp. 1-12, Wiley Periodicals, Inc.

Sigma-Aldrich, 2,3-Dibromo-1-porpanol, Brochure, pp. 1-3.

* cited by examiner

BROMINATED FLAME RETARDANTS AND POLYURETHANES CONTAINING THE SAME

CROSS-REFERENCE TO RELATED APPLICATIONS

This application is a 371 National Phase Entry of international application PCT/US2019/067750, filed Dec. 20, 2019 under the Patent Cooperation Treaty, which claims the benefit of U.S. Provisional Patent Application Ser. No. 62/785,483, filed Dec. 27, 2018, entitled "BROMINATED FLAME RETARDANT AND POLYURETHANE FOAMS CONTAINING THE SAME," the entire contents and substance of which are hereby incorporated by reference as if fully set forth below.

TECHNICAL FIELD

The various embodiments of the disclosure relate generally to compositions, processes, and methods for flame retardant polyurethanes and polyurethane foams. In particular, the flame retardant polyurethanes include brominated alkenyl alcohols.

BACKGROUND

Fire resistance is an important property of polyurethane materials, including polyurethane foams. Various compounds and mixtures have been used to meet applicable fire safety standards. For example, tris(1-chloro-2-propyl) phosphate (TCPP) is a flame retardant widely used in polyurethane foams. However, TCPP is a non-reactive compound in polyurethane foam formation and can leach out of or migrate from the foams. This can result in health and environmental concerns.

An isocyanate-reactive brominated compound, 2,3-dibromo-2-butene-1,4-diol, has been described in older patent literature (see e.g. U.S. Pat. No. 4,002,580). However, that compound requires additional processing steps in order to be effective. This group recently developed flame retardant polyurethanes that use a brominated alkenol, 2,3-dibromo-prop-2-en-1-ol (DBAA), for flame retardancy (see PCT/US2018/039578). Additional compounds that do not migrate out of polyurethane foams would be valuable to achieve flame retardancy without associated health and environmental concerns.

BRIEF SUMMARY

The various embodiments of the disclosure relate generally to compositions, process and methods for flame retardant polyurethanes, including polyurethane foams, containing brominated alkenols of Formula I below.

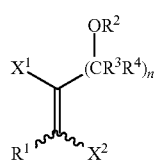

An embodiment of the disclosure can be a polyurethane comprising a compound of Formula I, wherein the compound of Formula I is chemically bonded in the polyurethane foam through at least one hydroxyl group on the compound;

Another embodiment of the disclosure can be a polyurethane formed from ingredients comprising a compound of Formula I. The polyurethane can further comprise at least one polyol and at least one isocyanate and/or polyisocyanate.

Another embodiment of the disclosure can be a process for forming a polyurethane, the process comprising contacting at least one isocyanate and/or polyisocyanate with a formulation comprising a compound of Formula I and at least one polyol; and allowing the mixture to cure to form a polyurethane.

Embodiments of the disclosure include the compound of Formula I below

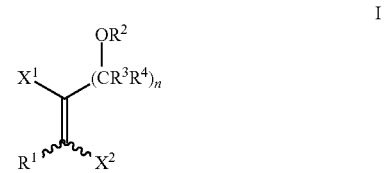

where $X^1$ and $X^2$ are each independently H, Cl, or Br, and at least one of $X^1$ or $X^2$ is Br; $R^1$ is H, Cl, Br, $C_1$-$C_4$ alkyl, or —$(CR^5R^6)_m$—$OR^7$; $R^2$ is H or $C_2$-$C_8$ alkylhydroxyl; $R^3$, $R^4$, $R^5$ and $R^6$ are each independently H, $C_1$-$C_8$ alkyl, $C_2$-$C_8$ alkenyl, $C_1$-$C_8$ haloalkyl or $C_2$-$C_8$ haloalkenyl; and $R^7$ is H, $C_1$-$C_8$ alkyl, $C_2$-$C_8$ alkenyl, $C_1$-$C_8$ haloalkyl, $C_2$-$C_8$ haloalkenyl or $C_2$-$C_8$ alkylhydroxyl. In the compound of Formula I, n can be 1 to 4, and m, when present, can be 1 to 4. The compound of Formula I does not include compounds where $R^2$ and $R^7$ both equal $C_2$-$C_8$ alkylhydroxyl when $X^1$=$X^2$=Br; and does not include the compounds 2,3-dibromoallyl alcohol or 2,3-dibromo-butene-1,4-diol.

In an embodiment of the disclosure, $R^2$ can be H. In another embodiment, $R^1$ can H. In another embodiment, $R^2$ can be H, n=1, and $R^3$ and $R^4$ can be H.

In an embodiment of the disclosure, n can be 1 and m, when present, can be 1.

In an embodiment of the disclosure, $X^1$ can be Br and $X^2$ can be Cl or H. Another embodiment can include $X^1$=Br, $X^2$=H, and $R^1$=H. Another embodiment can be where $X^1$, $X^2$ and $R^1$ are each Br.

In an embodiment of the disclosure, n can be 2-4. In other embodiments, n can be 2-4 and $R^2$ can be H.

In an embodiment of the disclosure, $R^2$ can be a $C_2$ to $C_8$ alkylhydroxyl.

In an embodiment of the disclosure, $R^1$ is H, and when one of $X^1$ and $X^2$ is Br, then the other is Cl. In another embodiment, when one of $X^1$ and $X^2$ is Br, then the other can be H.

DETAILED DESCRIPTION

Figure 1:
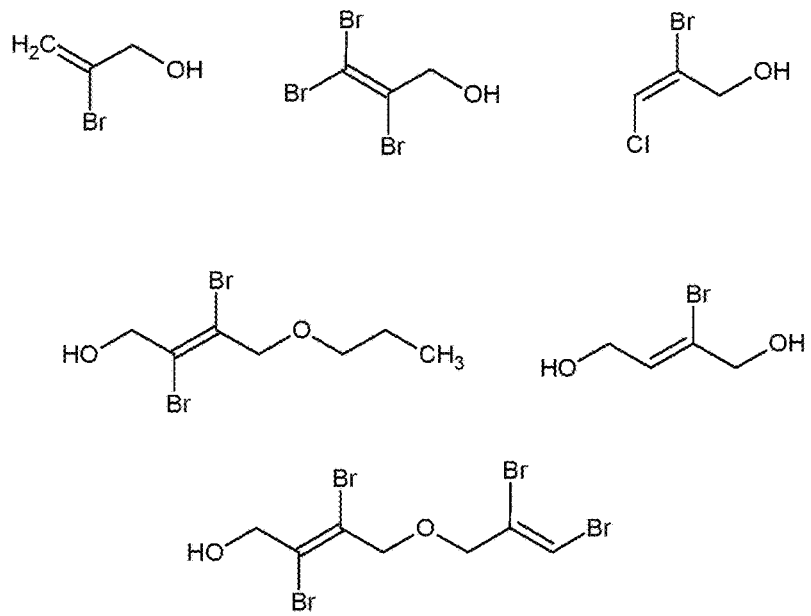
FIG. 1 illustrates compounds of Formula I in accordance with an exemplary embodiment of the disclosure.

Although preferred embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. The disclosure is capable of other embodiments and of being practiced or carried out in various ways.

It must also be noted that, as used in the specification and the appended claims, the singular forms "a," "an" and "the" include plural referents unless the context clearly dictates otherwise.

Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Ranges can be expressed herein as from "about" or "approximately" one particular value and/or to "about" or "approximately" another particular value. When such a range is expressed, another embodiment includes from the one particular value and/or to the other particular value.

By "containing" or "comprising" or "including" is meant that at least the named compound, element, particle, or method step is present in the composition or article or method, but does not exclude the presence of other compounds, materials, particles, method steps, even if the other such compounds, material, particles, method steps have the same function as what is named.

The term "alkyl", as used herein, unless otherwise indicated, includes saturated monovalent hydrocarbon radicals having straight or branched moieties. Examples of alkyl groups include, but are not limited to, methyl, ethyl, propyl, isopropyl, butyl, isobutyl, t-butyl, pentyl and hexyl.

The term "alkenyl", as used herein, unless otherwise indicated, includes alkyl moieties having at least one carbon-carbon double bond wherein alkyl is as defined above. Examples of alkenyl include, but are not limited to, ethenyl and propenyl.

The term "alkynyl", as used herein, unless otherwise indicated, includes alkyl moieties having at least one carbon-carbon triple bond wherein alkyl is as defined above. Examples of alkynyl include, but are not limited to, ethynyl, propynyl, and butynyl.

The term "alkoxy", as used herein, unless otherwise indicated, includes an —O— alkyl group, wherein alkyl is as defined above. Examples of alkoxy groups include, but are not limited to, methoxy, ethoxy, propoxy, isopropoxy, butoxy, isobutoxy, t-butoxy, pentoxy and hexoxy.

The term "alkylhydroxyl", as used herein, unless otherwise indicated, includes an alkyl-OH group, wherein the alkyl is as defined above. The —OH in the alkylhydroxyl can be on any of the carbons of the alkyl, producing primary secondary and tertiary hydroxyls, and can also include more than one hydroxyl in the alkylhydroxyl. Examples of alkylhydroxyl include, but are not limited to, —CH$_2$CH$_2$OH, —CH$_2$CH$_2$CH$_2$OH, —CH$_2$CH(OH)CH$_3$, —CH(OH) CH$_2$CH$_3$, and —CH$_2$C(CH$_3$)$_2$(OH). Other synonyms include C$_x$-C$_y$ hydroxyl, where x and y are integers, such as, for example, C$_1$ to C$_8$ hydroxyl.

The term "haloalkyl", as used herein, unless otherwise indicated, includes an alkyl containing one or more halogen atoms, wherein the alkyl is as defined above. The halogen atom in the haloalkyl can be on any of the carbons of the alkyl, producing primary, secondary and tertiary halogens, and can also include more than one halogen in the haloalkyl. Examples of haloalkyl include, but are not limited to, —CH$_2$CH$_2$X, —CH$_2$CH$_2$CH$_2$X, —CH$_2$CH(X)CH$_3$, —CH(X)CH$_2$CH$_3$, and —CH$_2$C(CH$_3$)$_2$(X), where X is F, Cl, Br or I. Other synonyms include halogenated C$_x$-C$_y$ alkyl, where x and y are integers, such as, for example, halogenated C$_1$ to C$_8$ alkyl.

The term "haloalkenyl", as used herein, unless otherwise indicated, includes an alkenyl containing one or more halogen atoms, wherein the alkenyl is as defined above. The halogen atom in the haloalkenyl can be on any of the carbons of the alkenyl, and can also include more than one halogen in the haloalkenyl. Examples of haloalkenyl include, but are not limited to, —CH=CHX, —CH$_2$CH=CHX, —CH$_2$C(X)=CH$_2$, and —CH(X)CH=CH$_2$, where X is F, Cl, Br or I. Other synonyms include halogenated C$_x$-C$_y$ alkenyl, where x and y are integers, such as, for example, halogenated C$_1$ to C$_8$ alkenyl.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Polyurethanes, including polyurethane foams, are typically produced by contacting two main liquid components, viz., polyisocyanates (A side) and polyols (B side). It is desirable for the B side which contains all of the components other than the polyisocyanates, to be in the form of a liquid. As used herein, the term "liquid" means that the formulation is in the liquid state at the conditions at which the B side formulation is used. For more information regarding the formation of polyurethane foams, see for example U.S. Pat. Nos. 3,954,684; 4,209,609; 5,356,943; 5,563,180; and 6,121,338. Thus, polyurethane generally refers to polymeric compositions composed of these isocyanates and polyols which can be cast, molded, or otherwise formed into a variety of structures and forms, and can be applied to numerous uses, including but not limited to rigid or flexible foams, elastomers, hard or flexible plastics, molded parts, and coatings. Flame retardancy in polyurethane foams is a particularly valuable area, as the foams can be especially flammable due to the porous microcellular nature of foams and are used in numerous applications, such as insulation in housing construction, cushions in upholstery, automotive seating, bedding, etc. Thus, flame retardancy of polyurethane foams is a particularly valuable area, but several other polyurethane applications can also benefit from flame retardancy. Polyurethanes of the present disclosure are not intended to be limited to only foams, and can be applicable to a range of polyurethane applications.

The present disclose relates to polyurethanes and polyurethane foams containing brominated alkenols, which can also be referred to herein as brominated alkenyl alcohols, or bromoalkenols. A brominated alkenol can react with an isocyanate to form a flame retardant polyurethane with the flame retardant bound directly to the polyurethane. These polyurethanes can be formed from formulations comprising the brominated alkenol and at least one polyol which can be contacted with a polyisocyanate to form the polyurethane.

The polyurethanes of the present disclosure can include a compound of Formula I, wherein the compound of Formula I can be chemically bonded in the polyurethane through at least one hydroxyl group on the compound. Similarly, the polyurethanes of the present disclosure can be formed from ingredients including a compound of Formula I.

The compound of Formula I can be described as

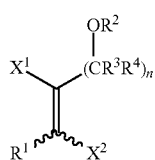

I wherein, $X^1$ and $X^2$ are each independently H, Cl or Br, and at least one of $X^1$ or $X^2$ is Br;

$R^1$ is H, Cl, Br, $C_1$-$C_8$ alkyl or —$(CR^5R^6)_m$—$OR^7$;

$R^2$ is H or $C_2$-$C_8$ alkylhydroxyl;

$R^3$, $R^4$, $R^5$ and $R^6$ are each H, $C_1$-$C_8$ alkyl, $C_2$-$C_8$ alkenyl, $C_1$-$C_8$ haloalkyl or $C_2$-$C_8$ haloalkenyl;

$R^7$ is H, $C_1$-$C_8$ alkyl, $C_2$-$C_8$ alkenyl, $C_1$-$C_8$ haloalkyl, $C_2$-$C_8$ haloalkenyl or $C_2$-$C_8$ alkylhydroxyl;

n=1-4; and m=1-4. The compound of Formula I does not include structures where $R^2$ is $C_2$-$C_8$ alkylhydroxyl, $X^1$=$X^2$=Br and $R^7$ is $C_2$-$C_8$ alkylhydroxyl; and does not include 2,3-dibromoallyl alcohol or 2,3-dibromo-butene-1,4-diol. Thus a proviso is that when $X^1$ and $X^2$ are both Br and n=1, then the compound cannot be 2,3-dibromoallyl alcohol or 2,3-dibromo-butene-1,4-diol. Another proviso is that $R^2$ and $R^7$ cannot both be $C_2$-$C_8$ alkylhydroxyl with $X^1$=$X^2$=Br.

As noted above, $R^2$ can be H or $C_2$-$C_8$ alkylhydroxyl. Preferably $R^2$ can be H or $C_2$-$C_4$ alkylhydroxyl. The disclosure can include $R^2$ equal to H, thus providing a hydroxyl group that can be bonded within the polyurethane foams. $R^2$ can also be a $C_2$-$C_8$ hydroxyl, which would then also provide a hydroxyl group that can be bonded within the polyurethane foams. Preferably $R^2$ is H.

As noted above, n can be 1-4. In some embodiments, n can be 2-4. In other embodiments, n can be 1-2, preferably 1.

As noted above, m when present can be 1-4. In some embodiments, m can be 2-4. In other embodiments, m can be 1-2, preferably 1.

As noted above $R^1$ can be H, Cl, Br, $C_1$-$C_8$ alkyl or —$(CR^5R^6)_m$—$OR^7$. The disclosure can have $R^1$ equal to H and the bromoalkenol can be a terminal alkene, with bromination along the alkene, with either or both of $X^1$ or $X^2$ equal to Br. When $R^1$ can be chlorine or bromine, the alkene can include a tri-halogenated alkene, including a tribrominated alkene having a high bromine content.

$R^1$ can alternatively be a $C_1$-$C_8$ alkyl or —$(CR^5R^6)_m$—$OR^7$, such that the alkene is not a terminal alkene. In some alternate embodiments, $R^1$ can be $C_1$-$C_4$ alkyl or —$(CR^5R^6)_m$—$OR^7$. $R^1$ can preferably be a —$(CR^5R^6)_m$—$OR^7$ and m can be 1-4, or preferably m=1. $R^7$ can be H, $C_1$-$C_8$ alkyl, $C_2$-$C_8$ alkenyl, $C_1$-$C_8$ haloalkyl, $C_2$-$C_8$ haloalkenyl or $C_2$-$C_8$ alkylhydroxyl. Preferably $R^7$ can be a $C_1$-$C_4$ alkyl, $C_2$-$C_4$ haloalkenyl or $C_2$-$C_4$ alkylhydroxyl.

As noted above, $R^3$, $R^4$, $R^5$ and $R^6$ can each independently be H, $C_1$-$C_8$ alkyl, $C_2$-$C_8$ alkenyl, $C_1$-$C_8$ haloalkyl or $C_2$-$C_8$ haloalkenyl. In some preferred embodiments, $R^3$, $R^4$, $R^5$ and $R^6$ can be each independently H or halogenated $C_2$-$C_4$ alkenyl, preferably H.

As noted above, $X^1$ and $X^2$ can each independently be H, Cl, or Br, when at least one of $X^1$ or $X^2$ is a bromine. Brominated compounds are well-recognized as effective flame retardant compounds, and bromination in one or both of the $X^1$ and/or $X^2$ positions, along with potentially $R^1$=Br, in this family of brominated alkenols has achieved excellent flame retardancy while also maintaining the important structural features of polyurethane foams, such as R value and dimensional stability.

Some non-limiting examples of isocyanate-reactive brominated alkenols are illustrated as FIG. 1. These include 2-bromoprop-2-en-1-ol (also referred to herein as bromoallyl alcohol or MBAA), 2,3,3-tribromoprop-2-en-1-ol (also referred to herein as tribromoallyl alcohol or TBAA), 2-bromo-3-chloroprop-2-en-1-ol (also referred to herein as bromochloroallyl alcohol or BCAA), 2-bromobut-2-en-1,4-diol (also referred to herein as MBBD), and 2,3-dibromo-4-propoxybut-2-en-1-ol (also referred to herein as DBPB). Brominated alkenol can be used in forming any polyurethane composition, including but not limited to both flexible polyurethane foams and rigid polyurethane foams. The brominated alkenol is a reactive component that becomes part of the polyurethane. This provides the advantage that isocyanate-reactive brominated flame retardant does not migrate out of the polyurethane. The brominated alkenol can also be selected to modify the bromine content in the polyurethane.

MBAA is a known molecule and it has CAS® registry number 598-19-6 (Chemical Abstracts Service). TBAA (2,3,3-tribromoallyl alcohol) is also a known molecule and it has CAS® registry number 758-85-0. MBBD (2-bromobut-2-en-1,4-diol) is also a known molecule and it has CAS® registry number 205440-83-1. BCAA (bromochloroallyl alcohol) and DBPB (2,3-dibromo-4-propoxybut-2-en-1-ol) are new compounds. Although many of these compounds are known they are not commercially available.

Some preferred embodiments of the polyurethane can include a compound of Formula I having one or more of:
wherein $R^2$ is H;
wherein $R^1$ is H;
wherein n is 1 and m, when present, is 1;
wherein $X^1$ is Br and $X^2$ is Cl or H;
wherein $X^1$ is Br, $X^2$ is H, and $R^1$ is H;
wherein $X^1$, $X^2$ and $R^1$ are each Br;
wherein n is 2-4, and $R^2$ is H;
wherein $R^2$ is a $C_2$ to $C_4$ hydroxyl; and/or
wherein $R_1$ is —$CH_2$—$OR^7$.

A preferred embodiment of a compound of Formula I can be where $R^2$ is H, n is 1, $R^1$ is —$CH_2OR^7$ and $R^7$ is $C_1$-$C_8$ alkyl, $C_1$-$C_8$ haloalkyl or $C_2$-$C_4$ haloalkenyl. A preferred embodiment may further have $X^1$ and $X^2$ as bromine.

A preferred embodiment of a compound of Formula I can be where $R^2$ is H and $R^1$, $X^1$ and $X^2$ are each independently Br or Cl. Another embodiment can be where $R^2$ is H and $R^1$, $X^1$ and $X^2$ are each Br.

A preferred embodiment of a compound of Formula I can be where $X^1$ is Br and $X^2$ is Cl or H, and $R^1$ is H, Cl, $C_1$-$C_4$ alkyl or —$(CR^5R^6)_m$—$OR^7$. Another embodiment can include where $X^1$ is H or Cl and $X^2$ is Br, and $R^1$ is H, Cl, $C_1$-$C_4$ alkyl or —$(CR^5R^6)_m$—$OR^7$.

A preferred embodiment of a compound of Formula I can be when one of $X^1$ or $X^2$ is Br, then the other is H, and $R^1$ is H.

A preferred embodiment of a compound of Formula I can be when $R^1$ is H, Cl, Br, or $C_1$-$C_4$ alkyl, and $R^2$ is a $C_2$ to $C_4$ alkylhydroxyl.

A preferred embodiment of a compound of Formula I can be 2-bromoprop-2-en-1-ol.

A preferred embodiment of a compound of Formula I can be 2,3-dibromo-4-propoxybut-2-en-1-ol.

A preferred embodiment of a compound of Formula I can be 2,3,3-tribromoprop-2-en-1-ol.

In the structure of Formula I, the stereochemistry of alkenyl groups across the double bond is unspecified, between the cis (Z) and trans (E) isomers. The synthetic routes to these compounds vary depending on the compound. Many of the compounds can be prepared by more than one synthetic route. For example, a common access route for the brominated alkene is a halogen addition across an alkyne bond. As one of ordinary skill might predict, the two groups $X^1$ and $X^2$ can end up trans to one another. However, as one of ordinary skill would appreciate, the selectivity of such a transformation is not necessarily 100%. Alternatively, some compounds can be made by a hydrogen halide elimination from a halogenated alkane. Such eliminations might lead to more cis-isomers, but can also depend on the stability of any intermediate specie. Regardless of what isomer is prepared by reactions that lead to a compound encompassed by Formula I, the cis and trans stereochemistry does not appreciably affect either the ability of the compound of Formula I to bond to polyurethanes or to the flame retardancy of that compound in the polyurethane.

Similarly, the regioselectivity of some reactions to place a bromine in either the $X^1$ or $X^2$ position does not affect the outcome of either the reactivity of the compound in preparing a foam or the flame retardancy of the foam. Thus, as a non-limiting example, bromochloroallyl alcohol can be prepared by addition of BrCl to propargyl alcohol. Bromine can typically end up in the $X^1$ position and chlorine in the $X^2$ position, but some portion of bromine can be in the $X^2$ position while chlorine can be in the $X^1$ position. Again, both regioisomers can be effective as polyurethane flame retardants.

Thus, another embodiment of a compound of Formula I can be a combination of compounds wherein a first compound has $X^1$ equal to Br, and $X^2$ equal to H, and a second compound has $X^1$ equal to H and $X^2$ equal to Br. Another embodiment of a compound of Formula I can be a combination of compounds wherein a first compound has $X^1$ equal to Br, and $X^2$ equal to Cl, and a second compound has $X^1$ equal to Cl and $X^2$ equal to Br.

Another embodiment of the disclosure can be a combination of more than one compound encompassed by Formula I.

The polyurethanes of the disclosure can also include an embodiment with a compound of Formula II can be described as

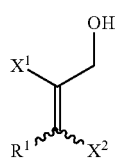

II wherein, $X^1$ and $X^2$ are each independently H, Cl, or Br, and at least one of $X^1$ or $X^2$ is Br;

$R^1$ is H, Cl, Br, $C_1$-$C_4$ alkyl, or —$(CR^5R^6)_m$—$OR^7$;

$R^5$ and $R^6$ are each independently H, $C_1$-$C_4$ alkyl, $C_2$-$C_4$ alkenyl, $C_1$-$C_4$ haloalkyl or $C_2$-$C_4$ haloalkenyl;

$R^7$ is H, $C_1$-$C_4$ alkyl, $C_2$-$C_4$ alkenyl, $C_1$-$C_4$ haloalkyl, $C_2$-$C_4$ haloalkenyl or $C_2$-$C_4$ alkylhydroxyl;

and m=1-4. The compound of Formula II does not include 2,3-dibromoallyl alcohol or 2,3-dibromo-butene-1,4-diol. Thus a proviso is that when $X^1$ and $X^2$ are both Br and n=1, then the compound cannot be 2,3-dibromoallyl alcohol or 2,3-dibromo-butene-1,4-diol.

As noted above, m can be 1-4. In some embodiments, m can be 2-4. In other embodiments, m can be 1-2, preferably 1.

As noted above $R^1$ can be H, Cl, Br, $C_1$-$C_4$ alkyl, or —$(CR^5R^6)_m$—$OR^7$. The disclosure can have $R^1$ equal to H, and the bromoalkenol can be a terminal alkene, with bromination along the alkene at either or both of $X^1$ or $X^2$. When $R^1$ can be chlorine or bromine, the alkene can include a tri-halogenated alkene, and including a tribrominated alkene having a high bromine content.

$R^1$ can alternatively be a $C_1$-$C_4$ alkyl, or —$(CR^5R^6)_m$—$OR^7$, such that the alkene is not a terminal alkene. $R^1$ can preferably be a —$(CR^5R^6)_m$—$OR^7$, and m can be 1-4, or preferably m=1. $R^7$ can be H, $C_1$-$C_4$ alkyl, $C_2$-$C_4$ alkenyl, halogenated $C_2$-$C_4$ alkenyl or $C_2$-$C_4$ hydroxyl. Preferably $R^7$ can be a $C_1$-$C_4$ alkyl, a halogenated $C_2$-$C_4$ alkenyl or $C_2$-$C_4$ hydroxyl.

As noted above, $R^5$ and $R^6$ can each independently be H, $C_1$-$C_4$ alkyl, $C_2$-$C_4$ alkenyl, $C_1$-$C_4$ haloalkyl or $C_2$-$C_4$ haloalkenyl. In some preferred embodiments, $R^5$ and $R^6$ can each independently be H or $C_2$-$C_4$ haloalkenyl, preferably H.

As noted above, $X^1$ and $X^2$ can each independently be H, Cl or Br, when at least one of $X^1$ or $X^2$ is a bromine. Brominated compounds are well-recognized as effective flame retardant compounds, and bromination in one or both of the $X^1$ and/or $X^2$ positions, along with potentially $R^1$, in this family of brominated alkenols has achieved excellent flame retardancy while also maintaining the important structural features of polyurethane foams, such are R value and dimensional stability.

Some preferred embodiments of the polyurethanes can include a compound of Formula II having one or more of:
wherein $R^1$ is H;
wherein m, when present, is 1;
wherein $X^1$ is Br and $X^2$ is Cl or H;
wherein $X^1$ is Br, $X^2$ is H, and $R^1$ is H;
wherein $X^1$, $X^2$ and $R^1$ are each Br; or
wherein $R^2$ is a $C_2$ to $C_4$ hydroxyl.

A preferred embodiment of a compound of Formula II can be where $R^1$ is —$CH_2OR^7$, and $R^7$ is $C_1$-$C_4$ alkyl, $C_1$-$C_4$ haloalkyl or $C_2$-$C_4$ haloalkenyl. A further preferred embodiment can further have $X^1$ and $X^2$ as bromine.

A preferred embodiment of a compound of Formula II can be where $R^1$, $X^1$ and $X^2$ are each independently Br or Cl. Another embodiment can be where $R^1$, $X^1$ and $X^2$ are each Br.

A preferred embodiment of a compound of Formula II can be where $X^1$ is Br and $X^2$ is Cl or H, and $R^1$ is H, Cl, $C_1$-$C_4$ alkyl, or —$(CR^5R^6)_m$—$OR^7$. Another embodiment can include where $X^1$ is H or Cl and $X^2$ is Br, and $R^1$ is H, Cl, $C_1$-$C_4$ alkyl, or —$(CR^5R^6)_m$—$OR^7$.

A preferred embodiment of a compound of Formula II can be when one of $X^1$ or $X^2$ is Br, then the other is H, and $R^1$ is H.

A preferred embodiment of a compound of Formula II can be 2-bromoprop-2-en-1-ol.

A preferred embodiment of a compound of Formula II can be 2,3-dibromo-4-propoxybut-2-en-1-ol.

A preferred embodiment of a compound of Formula II can be 2,3,3-tribromoprop-2-en-1-ol.

In the structure of Formula II, the stereochemistry and regiochemistry of alkenyl groups across the double bond can be as described above for Formula I.

Formulations containing the compound of Formula I and/or II as set forth above can be used as the B side formulation in processes for forming polyurethanes. The B side formulation can comprise a compound of Formula I and/or II and a polyol. The B side formulation can further comprise a blowing agent, a catalyst, and a surfactant.

In forming polyurethanes of the disclosure, a flame retardant amount of the compound of Formula I and/or II can be used. By a flame retardant amount is meant that amount of the compound needed to obtain the desired level of flame retardancy. A flame retardant amount can typically be in the range of about 1 wt % to about 25 wt %, preferably about 3 wt % to about 20 wt %, more preferably about 3 wt % to about 18%, based on the total weight of the formulation of B side components.

The polyol or polyols used in forming the polyurethane in the practice of this disclosure can be any polyol that is typically used to produce polyurethanes, such as flexible polyurethane foams or rigid polyurethane foams. Often, mixtures of polyols are used, with the particular polyols selected for their effect on the properties of the polyurethane foam being formed.

When flexible polyurethane foam is being formed, the polyol usually is a polyol or mixture of polyols having hydroxyl numbers up to about 150 mg KOH/g, preferably in the range of about 5 mg KOH/g to about 150 mg KOH/g, more preferably about 10 to about 100 mg KOH/g, even more preferably about 20 mg KOH/g to about 75 mg KOH/g. When polymeric polyols are used, they typically have molecular weights in the range of about 2,000 to about 10,000, preferably about 3,000 to about 8,000.

When rigid polyurethane foam is being formed, the polyol usually is a polyol or mixture of polyols having hydroxyl numbers in the range of about 150 to about 850 mg KOH/g, preferably in the range of about 200 to about 600 mg KOH/g. When polymeric polyols are used, they typically have molecular weights in the range of about 250 to about 5000, preferably about 400 to about 3000.

Suitable polyols for forming polyurethanes include polyether polyols, polyester polyols, aliphatic polyols, and polyoxyalkylene glycols. Mixtures of two or more polyols can be used. Preferred polyols for forming rigid polyurethane foams include polyester polyols.

Polyoxyalkylene glycols that can be used include polyoxyethylene glycol, polyoxypropylene glycol, and block and heteric polyoxyethylene-polyoxypropylene glycols.

The aliphatic polyols typically contain up to about 18 carbon atoms per molecule. Suitable aliphatic polyols include ethylene glycol, propylene glycol, the isomeric butylene glycols, diethylene glycol, 1,5-pentanediol, 1,6-hexanediol, triethylene glycol, glycerol, trimethylolethane, trimethylolpropane, 1,2,6-hexanetriol, pentaerythritol, tetraethylene glycol, dipentaerythritol, sorbitol, sucrose, and alpha-methylglycoside.

Polyether polyols are produced by reacting one or more alkylene oxides having 2 to about 8 carbons in the alkylene radical with an initiator molecule containing two or more hydroxyl groups. Suitable polyether polyols include sucrose/glycerine polyether polyol; sucrose polyether polyol based on glycerine, propylene oxide and ethylene oxide; glycerin-initiated polyether polyols, e.g., glycerine/propylene oxide polyether polyol; and mannich-based polyether polyols.

Polyester polyols are produced by polymerizing polycarboxylic acids or their derivatives, for example their acid chlorides or anhydrides, with a polyol. Suitable polyester polyols include aromatic polyester polyols and diethylene glycol-phthalic anhydride polyester polyol.

For forming polyurethanes, including both flexible and rigid polyurethane foams, the amount of polyol typically ranges from about 40 wt % to about 80 wt %, and often from about 50 wt % to about 70 wt %, based on the total weight of the B side components (formulation). These amounts refer to the total amount of polyol in the formulation, when there is more than one polyol present.

Blowing agents that can be used in this disclosure for forming flexible and rigid polyurethane foams include water, volatile hydrocarbons, hydrocarbons such as n-pentane, isopentane, cyclopentane; halocarbons (fully halogenated chlorofluorocarbons), in particular trichlorofluoromethane (CFC-11); and halohydrocarbons (hydrogen-containing chlorofluorocarbons, or HCFC's) such as 1,1-dichloro-1-fluoroethane (HCFC-141b), 1-chloro-1,1-difluoroethane (HCFC-142b), chlorodifluoromethane (HCFC-22). Mixtures of any two or more blowing agents can be used. In some instances, some alkenols can permit formulations in which water is the only blowing agent.

Other suitable blowing agents in the practice of this disclosure when forming flexible polyurethane foams include dichloromethane (methylene chloride) and acetone. Preferred blowing agents for flexible polyurethane foams include water. The amount of blowing agent for forming flexible foams may range from about 0.5 wt % to about 20 wt %, preferably about 2.5 wt % to about 15 wt %, based on the total weight of the B side components (formulation).

For forming rigid polyurethane foams, blowing agents which can be used in the practice of this disclosure include partially fluorinated hydrocarbons (HFC's). Suitable blowing agents for rigid foams include trans-1-chloro-3,3,3-trifluoropropene (HFO-1233zd(E)), 1,1,1,3,3-pentafluoropropane (HFC-245fa), 1,1,1,2-tetrafluoroethane (HFC-134a), 1,1,1,3,3,3-hexafluoropropane (HFC-236fa), 1,1,2,3,3,3-hexafluoropropane (HFC-236ea), and 1,1,1,4,4,4-hexafluorobutane (HFC-356mffm), and, and mixtures of any two or more of the foregoing. Preferred blowing agents when forming rigid foams include water, 1,1,1,3,3-pentafluoropropane, trans-1-chloro-3,3,3-trifluoropropene, and mixtures of water with 1,1,1,3,3-pentafluoropropane or trans-1-chloro-3,3,3-trifluoropropene. The amount of blowing agent for forming rigid foams may range from about 0.5 wt % to about 20 wt %, preferably about 2.5 wt % to about 15 wt %, based on the total weight of the B side components.

Various types of catalysts can be used in the practice of this disclosure when forming either flexible or rigid polyurethanes, including tertiary amines, tin catalysts, typically an organic tin compound, bismuth catalysts, other organometallic catalysts, and potassium salts of organic carboxylic acids. Mixtures of catalysts of the same type and/or different types can be used in the practice of this disclosure.

In the amine catalysts, the groups on the amine are preferably alkyl groups; more preferably, the groups are oxygen-containing groups such as etheric or saturated alcoholic groups. Suitable amine catalysts include dimethylethyl amine, triethylenediamine, propylenediamine, dimethylethylamine, dimethylcyclohexylamine, dimethylbenzylamine, tetramethyldipropylentriamine, pentamethyldiethylenetriamine, tris(dimethylaminopropyl)-hydrotriazine, 1-methyl-4-dimethylaminoethylpiperazine, 1,4-diaza(2,2,2)bicyclooctane, 3-methoxypropyldimethylamine, N-methylmorpholine, N-ethylmorpholine, N-cocomorpholine, bis(dimethylaminoethyl) ether, and ethanol amine catalysts, such as dimethylethanolamine, diethylethanolamine, 2-(2-dimethylaminoethoxy)ethanol, and N,N,N'-trimethylaminoethylethanol amine. For flexible foams, preferred catalysts include 2-(2-dimethylaminoethoxy)ethanol. For rigid polyurethane foam, the amine catalyst is preferably a tertiary amine.

Types of tin compounds that can be used as catalysts include dialkyl(dialkylthio) stannanes, stannous(II) salts of organic carboxylic acids, and dialkyltin(IV) salts of carboxylic acids. Suitable tin catalysts in the practice of this disclosure include dibutylbis(dodecylthio) stannane, stannous(II) octoate, stannous(II) acetate, dibutyltin dilaurate, and dioctyltin diacetate.

Still another type of catalyst is one or more potassium salts of organic carboxylic acids. Suitable potassium salts include potassium acetate and potassium octoate.

The catalysts are usually used in a total amount of about 0.25 wt % to about 10 wt %, preferably about 1 wt % to about 8 wt %, based on the total weight of the formulation (B side components) for both the flexible and rigid polyurethane foams. These amounts refer to the total amount of catalyst in the formulation, when there is more than one catalyst present.

A surfactant is often needed for production of polyurethane and polyurethane foams, and surfactants are normally used when forming both flexible and rigid polyurethane foams.

Suitable silicone-based surfactants include silicone glycols, silicone glycol copolymers, polyether modified polysiloxanes, polyether modified dimethylpolysiloxanes such as a polyether polydimethylsiloxane copolymer, polysiloxane polyoxoalkylene copolymers, polysiloxane polyoxoalkylene copolymers, polysiloxane copolymers, and the like. Silicone-based surfactants are a preferred type of surfactant for forming both flexible and rigid polyurethane foams. Polyether modified dimethylpolysiloxanes and polysiloxane copolymers are preferred silicone-based surfactants.

Cell openers, typically polyalkylene oxides, are a preferred type of surfactant for flexible foams. Suitable polyalkylene oxide cell openers in the practice of this disclosure include polyethylene glycol monoallyl ether, polyethylene glycol allyl methyl diether, polyethylene glycol monoallyl ether acetate, polyethylene glycol monomethyl ether, polyethylene glycol glycerol ether, polyethylene-polypropylene glycol monoallyl ether, polyethylene-polypropylene glycol monoallyl monomethyl diether, and polyethylene-polypropylene glycol allyl ether acetate.

Other surfactants that can be used when forming rigid polyurethane foams include emulsifiers such as sodium salts of castor oil sulfates or fatty acids; fatty acid salts with amines, e.g., diethylamine oleate and diethanolamine stearate; salts of sulfonic acids, e.g., alkali metal or ammonium salts of e.g., dodecylbenzenedisulfonic acid and ricinoleic acid; ethoxylated alkylphenols, ethoxylated fatty alcohols; ether amine quaternary ammonia compounds; 2-hydroxypropyltrimethylammonium formate; sodium hydroxy-nonylphenyl-N-methylglycinate (the sodium salt of N-((2-hydroxy-5-nonylphenyl)methyl)-N-methyl-glycine), and castor oil.

The surfactants are usually used in amounts of about 0.1 wt % to about 5 wt %, preferably about 0.5 wt % to about 5 wt %, based on the total weight of the B side components (formulation). These amounts refer to the total amount of surfactant in the formulation, when there is more than one surfactant present.

One or more optional additives which can be included in the formulation of the disclosure include antioxidants, diluents, chain extenders or cross-linkers, synergists (preferably melamine), stabilizers, fungistats, pigments, dyes, fillers, antistatic agents, and plasticizers.

The components of the formulation can be combined in any order; preferably, the blowing agent is the last ingredient added. Preferably, the compound of Formula I is combined with the polyol(s), followed by the surfactant, catalyst, and any optional ingredients, followed by the blowing agent.

The isocyanates or polyisocyanates (A-side component) used in forming the polyurethane in the practice of this disclosure can be any isocyanate or polyisocyanate that can be used to produce polyurethanes, including flexible polyurethane foams or rigid polyurethane foams, as appropriate. When a polymeric polyisocyanate is used, it preferably has an isocyanate (NCO) content of about 25 wt % to about 50 wt %, preferably about 25 wt % to about 40 wt %.

When forming flexible polyurethane foams, the isocyanate generally has at least two isocyanate groups. The isocyanates can be aliphatic or aromatic. When forming rigid polyurethane foams, polyisocyanates are used, and the polyisocyanate can be aromatic or aliphatic. Suitable polyisocyanates for both flexible and rigid polyurethane foams in the practice of this disclosure include, but are not limited to, 1,4-tetramethylene diisocyanate, 1,5-pentamethylene diisocyanate, 2-methyl-1,5-pentamethylene diisocyanate, 1,6-hexamethylene diisocyanate (HMDI), 1,7-heptamethylene diisocyanate, 1,10-decamethylene diisocyanate, cyclohexylene diisocyanate, isophorone diisocyanate (IPDI), 4,4'-methylenedicyclohexyl diisocyanate (H12MDI), hexahydrotoluene diisocyanate and isomers thereof, 2,2,4-trimethylhexamethylene diisocyanate, 2,4,4-trimethylhexamethylene diisocyanate, 4,4'-methylenebis(cyclohexylisocyanate), phenylene diisocyanate, toluene diisocyanate (TDI), xylene diisocyanate, other alkylated benzene diisocyanates, toluene diisocyanate, 1,5-naphthalene diisocyanate, diphenylmethane diisocyanate (MDI, sometimes called methylene diisocyanate), 1-methoxyphenyl-2,4-diisocyanate, 4,4'-diphenylmethane diisocyanate, 2,4'-diphenylmethane diisocyanate, mixtures of 4,4'- and 2,4-diphenylmethane diisocyanate, 4,4'-biphenylene diisocyanate, 3,3'-dimethoxy-4,4'-biphenyl diisocyanate, 3,3'-dimethyl-4,4'-biphenyl diisocyanate, 4,4',4''-triphenylmethane triisocyanate, toluene 2,4,6-triisocyanate, 4,4'-dimethyldiphenylmethane-2,2',5,5'-tetraisocyanate, polymeric polyisocyanates such as polymethylene polyphenylene polyisocyanate, and mixture of any two or more of the foregoing.

Polyisocyanates that can be used in forming both the flexible and rigid polyurethane foams of the present disclosure include those isocyanates commonly referred to as polymeric methylene diphenyl diisocyanate (MDI), polyisocyanate-based prepolymers, and mixtures thereof. Polymeric MDI contains varying amounts of isomeric diphenylmethane diisocyanates and three-ring, four-ring, and greater than four-ring oligomers. In general, any commercial polymeric MDI having an isocyanate content of about 25 wt % or more may be used. A preferred polymeric MDI has an isocyanate content of about 30 wt % or more. Other isocyanates may be present with the polymeric MDI in minor amounts, as long as the polyisocyanate mixture as whole remains liquid. Preferably, the polyisocyanate is a polymeric MDI.

The polyurethane compositions of this disclosure are formed from A side and B side components in which the A side is one or more isocyanates or polyisocyanates as described above, and the B side comprises a formulation of the disclosure. The polyurethane formation reaction generally occurs readily at room temperature; normally, the A side and the B side begin to react with each other as soon as they are in contact, and continue to react (cure), forming a polyurethane. Often, the mixture of the A side and B side is sprayed or cast to form a polyurethane.

Thus an embodiment of the disclosure includes processes for forming polyurethanes comprising contacting A) at least one isocyanate and/or polyisocyanate with B) a formulation comprising a compound of Formula I and at least one polyol; wherein the compound of Formula I is

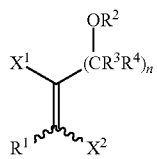

I wherein, $X^1$ and $X^2$ are each independently H, Cl or Br, and at least one of $X^1$ or $X^2$ is Br;

$R^1$ is H, Cl, Br, $C_1$-$C_8$ alkyl or —$(CR^5R^6)_m$—$OR^7$;

$R^2$ is H or $C_2$-$C_8$ alkylhydroxyl;

$R^3$, $R^4$, $R^5$ and $R^6$ are each H, $C_1$-$C_8$ alkyl, $C_2$-$C_8$ alkenyl, $C_1$-$C_8$ haloalkyl or $C_2$-$C_8$ haloalkenyl;

$R^7$ is H, $C_1$-$C_8$ alkyl, $C_2$-$C_8$ alkenyl, $C_1$-$C_8$ haloalkyl, $C_2$-$C_8$ haloalkenyl or $C_2$-$C_8$ alkylhydroxyl;

n=1-4; and m=1-4. The compound of Formula I does not include structures where $R^2$ is $C_2$-$C_8$ alkylhydroxyl, $X^1$=$X^2$=Br and $R^7$ is $C_2$-$C_8$ alkylhydroxyl; and does not include 2,3-dibromoallyl alcohol or 2,3-dibromo-butene-1,4-diol. Thus a proviso is that when $X^1$ and $X^2$ are both Br and n=1, then the compound cannot be 2,3-dibromoallyl alcohol or 2,3-dibromo-butene-1,4-diol. Another proviso is that $R^2$ and $R^7$ cannot both be $C_2$-$C_8$ alkylhydroxyl with $X^1$=$X^2$=Br.

The process can further comprise at least one blowing agent, at least one catalyst, and at least one surfactant in the (B) formulation with the compound of Formula I and the at least one polyol.

The compound of Formula I in the process can be further described in an analogous manner as with paragraphs [0037]-[0055] disclosed above.

The amount of isocyanates and/or polyisocyanate may be defined in terms of the Isocyanate Index.

Isocyanate Index =

$$\frac{\text{Actual equivalent amount of isocyanate used}}{\text{Theoretical equivalent amount of isocyanate needed}} \times 100$$

The theoretical equivalent amount of isocyanate is equal to one equivalent of isocyanate per one equivalent of reactive hydrogens from the B side. In the processes of this disclosure, Isocyanate Index values typically range from 80 to 200 or about 90 to about 150. Rigid polyurethane foams are usually formed by bringing together polyisocyanates with compounds having isocyanate-reactive hydrogen atoms (e.g., hydroxyl groups) in amounts such that the Isocyanate Index is in the range of about 85 to about 1000, preferably from about 95 to about 400, more preferably about 95 to about 200.

To form polyurethanes, the functionality (i.e., average number of hydroxyl groups per molecule), of the formulation (B side) which is typically provided by the polyol or mixture of polyols, is usually about 2 or more, preferably about 2 to about 8; more preferably about 3 or more, especially about 3 to about 8, more especially about 3 to about 7. For example, an alkenol with one hydroxyl has a functionality of one (i.e., one hydroxyl group in the molecule), which is chain-terminating, so at least a portion of the polyols in the formulation have three or more hydroxyl groups per molecule to form the polyurethane. The hydroxyl functionality is included in the calculation of the average functionality of the B side.

The flexible polyurethane foams formed in this disclosure have a density range of about 0.5 to about 1.0 lb/ft³ (8 to 16 kg/m³). The rigid polyurethane foams formed in this disclosure have a density range that varies with the end use application. For insulation foams, the density range is about 0.4 lb/ft³ to about 6.24 lb/ft³ (6.3 kg/m³ to 100 kg/m³), preferably about 1.56 lb/ft³ to about 5.0 lb/ft³ (25 kg/m³ to 80 kg/m³), and more preferably about 1.8 lb/ft³ to about 3.0 lb/ft³ (28.8 kg/m³ to 48.1 kg/m³).

Flexible polyurethane foams are typically used to form articles such as molded foams, slabstock foams, and may be used as cushioning material in furniture and automotive seating, in mattresses, as carpet backing, as hydrophilic foam in diapers, and as packaging foam.

The disclosure also includes novel compositions containing a compound of Formula III

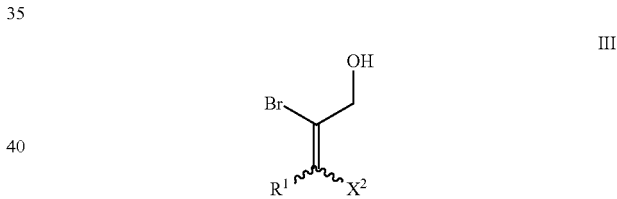

III wherein, $X^2$ is H, Cl, or Br;

$R^1$ is H or —$(CR^5R^6)_m$—$OR^7$; with the proviso that $R^1$ can only be H if $X^2$ is Cl;

$R^5$ and $R^6$ are each independently H, $C_1$-$C_4$ alkyl, $C_2$-$C_4$ alkenyl, $C_1$-$C_4$ haloalkyl or $C_2$-$C_4$ haloalkenyl;

$R^7$ is H, $C_1$-$C_8$ alkyl, $C_2$-$C_8$ alkenyl, $C_1$-$C_8$ haloalkyl, $C_2$-$C_8$ haloalkenyl or $C_2$-$C_8$ alkylhydroxyl;

and m=1-4; with the proviso that $X^2$ cannot be Br if $R^1$ is —$CH_2OH$.

In the compound of Formula III, $R^1$ can be —$(CR^5R^6)_m$—$OR^7$, preferably —$CH_2OR^7$.

In the compound of Formula III, $R^7$ can be H, $C_1$-$C_8$ alkyl, $C_2$-$C_8$ alkenyl, $C_1$-$C_8$ haloalkyl, $C_2$-$C_8$ haloalkenyl or $C_2$-$C_8$ alkylhydroxyl; more preferably $C_1$-$C_4$ alkyl, $C_2$-$C_4$ alkenyl, $C_1$-$C_4$ haloalkyl, $C_2$-$C_4$ haloalkenyl or $C_2$-$C_4$ alkylhydroxyl; even more preferably more preferably $C_1$-$C_4$ alkyl or $C_2$-$C_4$ haloalkenyl.

In the compound of Formula III, $R^5$ and $R^6$ can be each independently H, $C_1$-$C_4$ alkyl, $C_2$-$C_4$ alkenyl, $C_1$-$C_4$ haloalkyl or $C_2$-$C_4$ haloalkenyl; preferably H or $C_1$-$C_4$ alkyl, more preferably H.

In the compound of Formula III, m can be 1-4, preferably 1-2, more preferably 1.

In the compound of Formula III, $R^1$ can be —$CH_2OR^7$ and $R^7$ can be methyl, ethyl or propyl.

The disclosure can include compounds of Formula III, including bromochloroallyl alcohol and 2,3-dibromo-4-propoxybut-2-en-1-ol.

The following examples are presented for purposes of illustration, and are not intended to impose limitations on the scope of this disclosure. All percentages in the following examples are by weight unless otherwise noted.

EXAMPLES—GENERAL

In the Examples, some substances used are referred to acronyms or by their trade names. More specifically:
DBAA: 2,3-dibromoallyl alcohol
MBAA: 2-bromoprop-2-en-1-ol
TBAA: 2,3,3-tribromoprop-2-en-1-ol
MBBD: 2-bromobut-2-en-1,4-diol
DBPB: 2,3-dibromo-4-propoxybut-2-en-1-ol.
Voranol® 280: a polyether polyol with a functionality of about 7.0, a hydroxyl number of about 280, and an average molecular weight of about 1400; Voranol® 370: a sucrose/glycerine polyether polyol with a functionality of about 6.9 (all Voranol® materials are products of Dow Chemical Company).
Terate® HT 5349: an aromatic polyester polyol with a functionality of about 2.45, and a hydroxyl number of 295 to 315 (Invista Corporation).
Carpol® GSP-280: sucrose polyether polyol based on glycerine, sucrose, propylene oxide and ethylene oxide with a functionality of 7, a hydroxyl value of 280, and an average molecular weight of about 1400 (all Carpol® materials are products of Carpenter Company).
Dabco® DC193: silicone glycol surfactant; Dabco® T: amine with hydroxyl groups;
Dabco® T-120: dibutylbis(dodecylthio) stannane; Dabco® K-15: potassium octoate; (all Dabco® materials are products of Evonik Industries AG).
Polycat® 204: amine catalyst (Air Products and Chemicals, Inc).
Papi® 27: polymeric diphenylmethane diisocyanate (MDI) with 31.4 wt % NCO, viscosity 150 to 225 cps at 25° C., and an isocyanate equivalent weight of 134 (Dow Chemical Company).

Example 1

Figure 2:
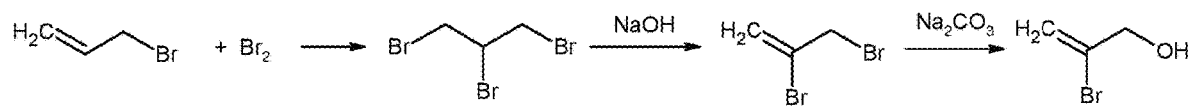
FIG. 2 illustrates a method of preparing a brominated alkenol in accordance with an exemplary embodiment of the disclosure.

An exemplary non-limiting synthesis of MBAA is shown in FIG. 2 and set forth here.

Allyl bromide (430 g) and dichloromethane (780 g) were cooled to less than 0° C. in a 2-L, 4-neck, jacketed, round-bottom reactor. Bromine ($Br_2$, 570 g) was added via a Mastedlex® L/S pump at a rate to maintain the reactor temperature at 0° C. for 2-2.5 hours. The reaction mixture was slowly warmed to 15-20° C. and the excess bromine was quenched with 10% aq. sodium thiosulfate solution (150 g). Removal of solvent from organic phase by rotary evaporation gave 1,2,3-tribrompropane (1005 g) as a light orange oil. Product was analyzed by GC and NMR.

1,2,3-Tribromopropane (805 g), deionized water (40 g), and sodium hydroxide pellets (200 g) were added to a 1-L, 3-neck, round-bottom reactor. Reactor was equipped with a distillation head and a distillate receiver. The mixture was heated with a heating mantle to 110° C. and the reaction temperature kept rising to 145-150° C. Heating was resumed when distillation stalled and pot temperature started decreasing. Final pot temperature was raised to 165° C. and slight vacuum was applied to remove more product from pot. Aqueous phase was cut from collected distillate to give the crude 2,3-dibromopropene (580 g). Product was analyzed by GCMS, GC, and NMR. GC analysis showed 95.6 area % of dibromopropene (including 2 minor isomers) and 4.4 area % of 1,2,3-tribromopropane.

Sodium carbonate (205 g), deionized water (1845 g), 2,3-dibromopropene (362 g), and tetrabutylammonium bromide (0.5 g) were agitated in a 3-L, 4-neck, round-bottom reactor. The mixture was heated at 90-95° C. for 2 hours and GC analysis of a sample showed complete conversion. The reaction mixture was cooled to 30° C. and the bottom organic phase (88 g) was collected. Sodium carbonate (200 g) and 2,3-dibromopropene (360 g) were added to the pot and the reaction mixture was heated at 92-94° C. for 3 hours or until complete conversion by GC. The reaction mixture was cooled to 60° C. and the bottom organic phase (260 g) was collected. The aqueous phase was cooled to 38-40° C. and extracted with dichloromethane (2×350 mL). The combined organic layers were concentrated by rotary evaporation to give the crude MBAA (465 g) as a brown liquid.

Purification of crude 2-bromoallyl alcohol (525 g) by vacuum distillation over a 10-plate Older-Shaw column afforded MBAA (439 g) as a light yellow liquid. GC analysis indicated >99% purity included isomers.

Figure 3:
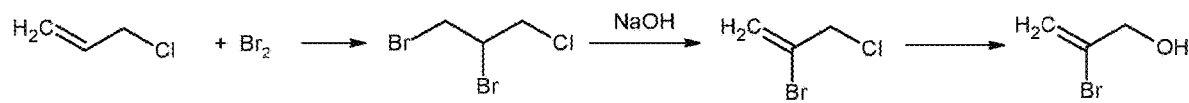
FIG. 3 illustrates a method of preparing a brominated alkenol in accordance with an exemplary embodiment of the disclosure.

An alternative synthesis of MBAA is shown in FIG. 3, where the starting material can be allyl chloride.

Example 2

Figure 4:
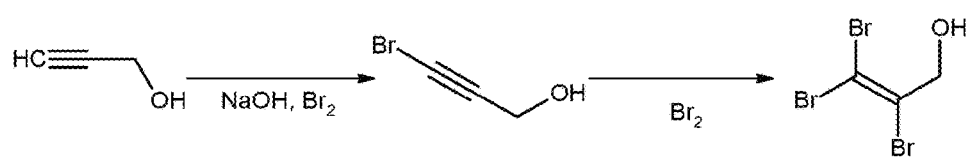
FIG. 4 illustrates a method of preparing a brominated alkenol in accordance with an exemplary embodiment of the disclosure.

An exemplary non-limiting synthesis of TBAA is shown in FIG. 4 and set forth herein.

NaOH solution was prepared by dissolving NaOH pellets (102 g) in deionized water (205 g) in a 2-L, jacketed, 5-neck, round-bottom reactor. The caustic solution was agitated and cooled to <0° C. Propargyl alcohol (75 g) was added at 0° C. over 15 minutes and the line was rinsed with water (20 g). $Br_2$ (240 g) was added via a Masterflex® L/S pump at a rate to maintain the reactor temperature at −3° C. After the bromine addition finished, the reaction mixture was slowly warmed to 10° C. over a period of 2 hours. The reaction mixture was extracted with dichloromethane (200 mL). Phase separation gave 470 g of organic phase and 435 g of aqueous phase. The organic phase was used for the following bromination step.

The combined organic layers from four experiments were neutralized with 48% HBr solution in a 3-L, 4-neck, jacketed, round-bottom reactor. The mixture was cooled to 10° C. and $Br_2$ (500 g) was added via a Masterflex® L/S pump at a rate to maintain the reactor temperature at 15° C. A heat kick along with solid formation was observed after about 400 g of bromine was added. Dichloromethane (900 g) was added to dissolve the solids and addition of bromine was then resumed. GC analysis indicated complete conversion. Excess bromine was quenched with 5% thiosulfate solution and pH value was adjusted to 6-7 if necessary. Phase separation and removal of solvent gave 850 g of crude 2,3,3-tribromoprop-2-en-1-ol.

Purification: The crude TBAA product and dichloromethane (800 mL) was heated to refluxing and the mixture was filtered to remove the solids. The cake was washed with dichloromethane (100 mL) and the combined filtrates were concentrated by a rotary evaporator to a thick slurry. Filtration and rinse of cake with light petroleum ether yielded white crystalline solids. Recovering more product from filtrate by repeating the process twice gave three crops of wet cakes. Drying under vacuum oven at 45° C. gave 650 g of TBAA as a white crystalline solid. Purified product was analyzed by GC and NMR. Product purity was 99.5 area % by GC.

Example 3

An exemplary non-limiting synthesis of 2,3-dibromo-4-propoxybut-2-en-1-ol is set forth herein.

2,3-dibromobut-2-en-1,4-diol (98.4 g), toluene (150 g), and NaOH aqueous solution (25%, 70.4 g) were heated to 70° C. to dissolve the solids in a 1-L, 4-neck, round-bottom reactor. Aliquot HTA-1 (0.5 g) and 1-bromopropane (25.0 g) were added via a syringe. The reaction mixture was heated at 72° C. for 4 hours. The reactor temperature was cooled to 60° C. and the top toluene layer was decanted. Toluene was removed by vacuum to give the crude product (47.7 g) as a colorless oil. Crystals were formed upon cooling and standing. Filtering through a medium-fritted funnel yielded 2,3-dibromo-4-propoxybut-2-en-1-ol (42.5 g) as a colorless liquid. Product was analyzed by GC and NMR.

The aqueous layer in the reactor was diluted with deionized water (70 g) and acidified with 48% HBr to pH 2. The mixture was cooled to 35° C. and was then filtered. The filter cake was washed with water (100 g) and was dried to give the unreacted 2,3-dibromobut-2-en-1,4-diol (43.9 g).

Example 4

An exemplary non-limiting synthesis of 4-propoxybut-2-yn-1-ol is set forth herein.

Sodium hydroxide solution (40%, 110 g) was prepared by dissolving NaOH pellets (44 g) in deionized water (66 g) in a 1-L, 3-neck, round-bottom reactor. 2-Butyn-1,4-diol (86 g) and Aliquot HTA-1 (1.0 g) were added and the mixture was agitated to dissolve the solids. Toluene (200 g) and 1-bromopropane (130 g) were added and the mixture was heated to refluxing at 72-74° C. for 6 hours. The reaction mixture was cooled to 25° C. and phase separation gave the organic phase (324 g). Evaporation of the organic phase yielded the crude product (63 g) as a light orange oil. Product was analyzed by GC and NMR.

The aqueous phase was returned to the reactor and NaOH (40 g), deionized water (70 g), 2-butyne-1,4-diol (86 g) were added. The mixture was agitated to dissolve the solids. Toluene (180 g) and 1-bromopropane (130 g) were added and the mixture was heated to refluxing at 72-74° C. for 6 hours. The reaction mixture was cooled to 25° C. and phase separation gave the organic phase (305 g). Evaporation of the organic phase yielded the crude product (80 g) as a light orange oil. Product was analyzed by GC and NMR.

The aqueous phase from the last experiment was returned to the reactor and deionized water (10 g) was added. Toluene (180 g) and 1-bromopropane (130 g) were added and the mixture was heated to refluxing at 72-74° C. for 6 hours. The reaction mixture was cooled to 20° C. to give a slurry. The mixture was filtered and the cake was washed with toluene (20 mL). Phase separation of the filtrate gave the organic phase (340 g). Evaporation of the organic phase yielded the crude product (45 g) as a brown oil. Product was analyzed by GC and NMR.

Example 5

An exemplary non-limiting synthesis of 4-propoxybut-2-yn-1-ol is set forth herein.

Sodium hydroxide solution (35%, 585 g) was prepared by dissolving NaOH pellets (205 g) in deionized water (380 g) in a 3-L, 4-neck, round-bottom reactor. 2-Butyne-1,4-diol (400 g) and Aliquot HTA (5.0 g) were added and the mixture was agitated to dissolve the solids. Toluene (900 g) and 1-bromopropane (605 g) were added and the mixture was heated to refluxing at 72-74° C. for 6 hours. The reaction mixture was cooled to 40° C. and phase separation gave the organic phase. Evaporation of the organic phase yielded the concentrate (245 g) as a light orange oil. Product was analyzed by GC.

The aqueous phase and distillate from the last experiment were returned to the reactor. The containers were rinsed with deionized water (20 g) and toluene (30 g) to the reactor. 1-Bromopropane (368 g) was added and the mixture was heated to refluxing at 72-74° C. for 6 hours. The reaction mixture was cooled to 25° C. and phase separation gave the organic phase. Evaporation of the organic phase yielded the concentrate (150 g) as a light orange oil. Product was analyzed by GC.

The aqueous phase and distillate from the last experiment were returned to the reactor. The mixture was heated to refluxing at 83-85° C. for 7 hours. The reaction mixture was cooled to 30° C. and phase separation gave the organic phase. Evaporation of the organic phase yielded the concentrate (114 g) as a brown oil. The combined concentrates were further stripped at 45° C./20 mmHg to give the crude product (483 g). Product was analyzed by GC and GCMS.

Purification of crude 4-propoxybut-2-yn-1-ol (654 g) by vacuum distillation over a 10-plate Older-Shaw column afforded the purified 4-propoxybut-2-yn-1-ol (434 g) as a light yellow liquid. GC analysis indicated 96.8 area % purity.

Example 6

An exemplary non-limiting synthesis of 2,3-dibromo-4-propoxybut-2-en-1-ol is set forth herein.

The purified 4-propoxybut-2-yn-1-ol (434 g) and dichloromethane (500 g) were placed in a 3-L, 4-neck, jacketed, round-bottom reactor. The mixture was cooled to −5° C. and $Br_2$ (540 g) was added via a Masterflex® L/S pump at a rate to maintain the reactor temperature at 0° C. over a period of 3 hours. GC analysis indicated complete conversion. After agitating at 0° C. for 30 minutes, the excess bromine was quenched with 2% thiosulfate solution (250 g). pH value was adjusted to 10-11 with 50% NaOH solution after bromine color discharged. Phase separation gave the organic phase (1480 g). Evaporation of solvent in vacuum and filtration yielded 2,3-dibromo-4-propoxybut-2-en-1-ol (936 g) as a clear brown liquid. Product was analyzed by GC and NMR. NMR analysis showed a mixture of mono-alkylated/di-alkylated product in 98.6:1.4 (w/w) ratio.

Examples 7-21

Cone calorimetry measurements were performed on a Fire Testing Technology Dual Cone calorimeter according to ASTM E-1354. For all of the Examples, an incident heat flux of 40 kW/m$^2$ was used in the cone calorimetry tests for the Predicted Smoke Index calculations and an incident heat flux of 100 kW/m$^2$ was used in the cone calorimetry tests for the Predicted Flame Spread Index calculations. The Peak Heat Release Rate (PHRR), the maximum value of the heat released during combustion of the sample in the cone calorimeter, was measured. Values for the Peak Heat Release Rate are preferably less than 250. The ASTM E-84 burn profiles for predicted Smoke Index calculations and for predicted Flame Spread Index calculations were calculated from the cone calorimetry results. Using mathematical equations that were previously derived from a cone calorimeter and ASTM E-84 correlation study, the cone calorimeter results were converted into predicted numbers in the ASTM E-84. The target value for the Flame Spread Index was less than 25, preferably less than 20, and the target value for the Smoke Density Index was less than 450, preferably less than 200. The term "Smoke Index" is short for "smoke density developed", which is also referred to as "Smoke Developed Index" and "Smoke Density Index."

For the dimensional stability, preferred volume changes in dimensional stability are ±15%. From the thermal conductivity test, and R values were calculated from the thermal conductivities. The R value (or R-value) is a measure of insulation efficiency or thermal resistance (the ability of a material to slow down heat transfer within itself), and is often used in the building and construction industry. The higher the R-value, the more a material prevents heat transfer. R-values for closed-cell polyurethane foams are preferably about 6.5/inch or more.

The reported results for all of the Examples are an average of three lots with 5 samples per lot (a total of 15 samples for each test). The volume ratio of the A side to the B side in each run was 1:1, unless otherwise noted. All of the polyurethane foams were prepared as described below. The A side was Papi® 27 in all runs.

To form the B side, the flame retardant, polyols, surfactants, flame retardant, water and catalyst (when used) were weighed into a 0.5 gallon (1.9 L) reclosable container, and blended with a bow-tie agitator at 2000 rpm for 60 seconds or until a homogenous mixture with no visible phase separation was obtained. At a 450-g scale (total of A and B sides), the required amount of the B side mixture was weighed and added to a one-liter paper cup.

The polymeric MDI was wet-tared by weighing about 10% of its required amount into a 250-mL paper cup, pouring out the polymeric MDI within 3 seconds, re-taring the wet 250-mL cup and adding the full amount of the polymeric MDI. The polymeric MDI was then poured within a 3-second time span into the one-liter cup containing the B-side mixture, and the contents of the one liter paper cup were immediately mixed for 5 seconds at 2000 rpm. By this process, the amount of MDI used is within ±1% of the required amount.

While the foam was rising but before the foam reached the top of the one liter paper cup, the cup was inverted and held over a paper sheet. While the foam continued to rise, the cup was guided upwards without impeding the rising of the foam. Once the foam had sufficient strength to support itself and the cup, guiding of the cup was discontinued. After allowing the foam to sit for at least 24 hours, it was cut to generate specimens for cone calorimeter testing. Each specimen was weighed to determine the foam density.

TABLE 1

| Example # | 7 | 8 | 9 | 10 | 11 | 12 | 13 | 14 |
|---|---|---|---|---|---|---|---|---|
| B-side Raw Materials | 9917-039 | 9917-188 | 9917-189 | 9917-190 | 9917-198 | 9917-199 | 9917-200 | 9946-004 |
| Terate ® HT5349 | 39.82 | 39.78 | 40.33 | 39.21 | 39.78 | 40.33 | 39.21 | 41.84 |
| Voranol ® 280 | — | — | — | — | 30.99 | 31.42 | 30.55 | — |
| Voranol ® 370 | 2.61 | — | — | — | — | — | — | — |
| Carpol ® GSP-280 | 28.39 | 30.99 | 31.42 | 30.55 | — | — | — | 32.60 |
| MBAA | — | — | — | — | 9.94 | 8.95 | 10.94 | — |
| DBAA | 10.42 | — | — | — | — | — | — | — |
| TBAA | — | 9.94 | 8.95 | 10.94 | — | — | — | 6.38 |
| MBBD | — | — | — | — | — | — | — | — |
| DBPB | — | — | — | — | — | — | — | — |
| Dabco ® DC193 | 1.94 | 2.00 | 2.00 | 2.00 | 2.00 | 2.00 | 2.00 | 2.00 |
| Dabco ® T-120 | 0.24 | 0.25 | 0.25 | 0.25 | 0.25 | 0.25 | 0.25 | 0.25 |
| Dabco ® K-15 | 0.24 | 0.25 | 0.25 | 0.25 | 0.25 | 0.25 | 0.25 | 0.25 |
| Polycat ® 204 | 3.88 | 4.00 | 4.00 | 4.00 | 4.00 | 4.00 | 4.00 | 4.00 |
| WATER | 0.82 | 0.80 | 0.80 | 0.80 | 0.85 | 0.85 | 0.85 | 0.79 |
| Opteon 1100 | 11.64 | 12.00 | 12.00 | 12.00 | 12.00 | 12.00 | 12.00 | 12.00 |
| B-side Viscosity cps @ 25° C. | 890 | 940 | 995 | 955 | 785 | 730 | 595 | 945 |
| A-side | % | % | % | % | % | % | % | % |
| Papi ® 27 | 100.00 | 100.00 | 100.00 | 100.00 | 100.00 | 100.00 | 100.00 | 100.00 |
| Processing | | | | | | | | |
| A:B Volume Ratio | 100:100 | 100:100 | 100:100 | 100:100 | 100:100 | 100:100 | 100:100 | 100:100 |
| A:B Weight Ratio | 0.989:1 | 0.983:1 | 0.989:1 | 0.977:1 | 1.047:1 | 1.050:1 | 1.043:1 | 1.005:1 |
| Isocyanate Index | 1.122 | 1.145 | 1.148 | 1.141 | 1.141 | 1.147 | 1.133 | 1.16 |

| Example # | 15 | 16 | 17 | 18 | 19 | 20 | 21 |
|---|---|---|---|---|---|---|---|
| B-side Raw Materials | 9946-005 | 9946-022 | 9946-023 | 9946-024 | 9946-025 | 9946-026 | 9946-027 |
| Terate ® HT5349 | 41.48 | 39.28 | 38.69 | 39.87 | 40.08 | 40.61 | 39.56 |
| Voranol ® 280 | — | 30.60 | 30.14 | 31.06 | 31.23 | 31.64 | 30.82 |
| Voranol ® 370 | — | — | — | — | — | — | — |
| Carpol ® GSP-280 | 32.32 | — | — | — | — | — | — |
| MBAA | — | — | — | — | — | — | — |
| DBAA | 6.91 | — | — | — | — | — | — |
| TBAA | — | — | — | — | — | — | — |
| MBBD | — | 10.81 | 11.87 | 9.75 | — | — | — |
| DBPB | — | — | — | — | 9.36 | 8.42 | 10.3 |
| Dabco ® DC193 | 2.00 | 2.00 | 2.00 | 2.00 | 2.00 | 2.00 | 2.00 |
| Dabco ® T-120 | 0.25 | 0.25 | 0.25 | 0.25 | 0.25 | 0.25 | 0.25 |
| Dabco ® K-15 | 0.25 | 0.25 | 0.25 | 0.25 | 0.25 | 0.25 | 0.25 |
| Polycat ® 204 | 4.00 | 4.00 | 4.00 | 4.00 | 4.00 | 4.00 | 4.00 |
| WATER | 0.79 | 0.82 | 0.81 | 0.82 | 0.83 | 0.83 | 0.83 |
| Opteon 1100 | 12.00 | 12.00 | 12.00 | 12.00 | 12.00 | 12.00 | 12.00 |

TABLE 1-continued

| | | | | | | | |
|---|---|---|---|---|---|---|---|
| B-side Viscosity cps @ 25° C. | 860 | 1150 | 1155 | 1080 | 885 | 890 | 785 |
| A-side | % | % | % | % | % | % | % |
| Papi ® 27 Processing | 100.00 | 100.00 | 100.00 | 100.00 | 100.00 | 100.00 | 100.00 |
| A:B Volume Ratio | 100:100 | 100:100 | 100:100 | 100:100 | 100:100 | 100:100 | 100:100 |
| A:B Weight Ratio | 1.008:1 | 1.039:1 | 1.035:1 | 1.043:1 | 1.047:1 | 1.050:1 | 1.044:1 |
| Isocyanate Index | 1.15 | 1.056 | 1.043 | 1.071 | 1.209 | 1.21 | 1.209 |

TABLE 2

| Example # | 7 | 8 | 9 | 10 | 11 | 12 | 13 | 14 |
|---|---|---|---|---|---|---|---|---|
| Foam Properties | | | | | | | | |
| % Br content in foam (calc'd) | 3.87 | 4.08 | 3.66 | 4.50 | 2.83 | 2.54 | 3.12 | 2.54 |
| Flame Spread Index | 19.9 | 20.0 | 19.7 | 18.5 | 19.3 | 20.0 | 18.5 | 20.7 |
| Smoke Density Index | 26 | 28 | 16 | 18 | 64 | 69 | 61 | 14 |
| Peak Heat Release Rate | 222 | 203 | 207 | 184 | 228 | 261 | 238 | 229 |
| Mass Loss (Tgt. <85%) | 88.5 | 92.3 | 91.9 | 91.9 | 92.0 | 92.8 | 91.8 | 92.8 |
| Dimensional Stability (% DV) | −4.72 | −0.41 | −0.28 | −0.12 | −4.35 | −4.69 | −3.87 | −0.49 |
| R-value/in. | 7.73 | 7.97 | 7.85 | 7.72 | 7.61 | 7.77 | 7.75 | 7.49 |
| Compressive Strength (psi) | 18.3 | ND | ND | ND | ND | ND | ND | ND |
| Free Rise Density (pcf) | 1.81 | 2.01 | 2.04 | 2.05 | 1.96 | 2.01 | 2.02 | 2.07 |

| Example # | 15 | 16 | 17 | 18 | 19 | 20 | 21 |
|---|---|---|---|---|---|---|---|
| Foam Properties | | | | | | | |
| % Br content in foam (calc'd) | 2.54 | 2.54 | 2.80 | 2.29 | 2.54 | 2.28 | 2.8 |
| Flame Spread Index | 20.8 | 18.9 | 17.8 | 20.1 | 19.0 | 21.0 | 19.8 |
| Smoke Density Index | 22 | 20 | 12 | 13 | 33 | 28 | 27 |
| Peak Heat Release Rate | 241 | 200 | 203 | 198 | 245 | 265 | 232 |
| Mass Loss (Tgt. <85%) | 92.4 | 89.3 | 89.4 | 89.2 | 90.0 | 90.4 | 89.3 |
| Dimensional Stability (% DV) | −1.75 | 0.79 | 0.10 | 1.40 | 0.42 | 0.81 | 0.75 |
| R-value/in. | 7.46 | 7.89 | 7.65 | 7.68 | 7.75 | 7.61 | 7.79 |
| Compressive Strength (psi) | ND | ND | ND | ND | ND | ND | ND |
| Free Rise Density (pcf) | 2.04 | 2.09 | 2.07 | 2.08 | 2.09 | 2.14 | 2.03 |

Example 22

Several dibromoalkenes and bromochloro alkenes can be prepared from the analogous alkynes by synthetic routes set forth in PCT/US2018/053401, the contents of which are incorporated by reference as if set forth in their entirety.

An exemplary non-limiting synthesis of 3,4-dibromobut-3-en-1-ol is set forth herein.

3-butyn-1-ol and dichloromethane can be cooled to less than 0° C. in a 4-neck, jacketed, round-bottom reactor. $Br_2$ can be added via a Mastedlex® L/S pump at a rate to maintain the reactor temperature at 5 to 7° C. The bath temperature can be initially set at −20° C. and then raised to −5° C. during the last 20% bromine addition. $K_2CO_3$ (aq., 40%, 30 g) can be added to mixture and phase separation can give an organic phase which can be stripped by a rotary evaporator to give 3,4-dibromobut-3-en-1-ol.

Example 23

An exemplary non-limiting synthesis of 3,4-dibromobut-3-en-2-ol is set forth herein.

3-butyn-2-ol alcohol and methanol can be cooled to less than 0° C. in a 4-neck, jacketed, round-bottom reactor. $Br_2$ can be added via a Mastedlex® L/S pump at a rate to maintain the reactor temperature at 3 to 5° C. The bath temperature was initially set at −20° C. and gradually raised to −10° C. After the bromine addition finished, the bath temperature was set at 0° C. $K_2CO_3$ (aq., 20%, precooled to 0 to 5° C., 75 g) can be added and the mixture can be warmed to 10° C. Phase separation can give an organic phase which can be separated and stripped by a rotary evaporator and then by vacuum to give 3,4-dibromobut-3-en-2-ol.

Example 24

An exemplary non-limiting synthesis of 2,3-(chlorobromo)-prop-2-en-1-ol is set forth herein.

Propargyl alcohol and dichloromethane can be cooled to less than 0° C. in a 4-neck, jacketed, round-bottom reactor. BrCl can be added via a Masterflex® L/S pump at a rate to maintain the reactor temperature at 5 to 7° C. The bath temperature can be initially set at −20° C. and then raised to −5° C. during the last 20% BrCl addition. $K_2CO_3$ (aq., 40%, 30 g) can be added to mixture and phase separation can give an organic phase which can be stripped by a rotary evaporator to give 2,3-(chlorobromo)-prop-2-en-1-ol in a combination of isomers.

Example 25

An exemplary non-limiting synthesis of MBAA is set forth herein.

2,3-dibromopropene (10.00 g) was added dropwise to a slurry of $K_2CO_3$ (11.07 g) in deionized water (30.0 g) in a 250 ml round bottom flask set up for reflux and magnetic stirring. The reaction mixture was heated to 95° C. for 6 hours. Upon cooling to room temperature, the light brown organic phase (5.02 g; isolated yield 73%) was separated and analyzed by GCMS and $^1$H-NMR.

Example 26

An exemplary non-limiting synthesis of 2,4-dibromo-2-buten-1-ol is set forth herein.

A four-neck 500 ml flask was set up with a fritted gas dispersion tube for anhydrous HBr addition, an outlet to a caustic scrubber, a temperature probe, and magnetic stirring. The flask was charged with dry tetraethylammonium bromide (37.0 g; 176 mmol; 1.5 equiv), dry CH$_2$Cl$_2$ (250 ml), and 2-butyn-1,4-diol (10.18 g; 118 mmol; 1 equiv.). HBr was fed for 2 h from a cylinder. During the course of the HBr feed the temperature rose from 23° C. to 35.7° C., and the insoluble flakes of 2-butyn-1,4-diol gradually disappeared as the CH$_2$Cl$_2$ solution darkened to a brown opaque color. After two hours the temperature began to drop and the HBr feed was discontinued. The apparatus was flushed with N$_2$ for two hours to purge residual HBr. To remove the TEAB, the solution was diluted to 1000 ml with diethyl ether and filtered on coarse sintered frit. The filtrate was condensed via rotary evaporation to yield 22.99 g of a brown liquid which was analyzed by $^1$H-NMR and GCMS and determined to be a mixture of 2,4-dibromo-2-buten-1-ol (80%) and 1,2,4-tribromobutene (20%).

Example 27

An exemplary non-limiting synthesis of 2,4-dibromo-2-buten-1-ol is set forth herein.

A four-neck 500 ml was set up with a fitted gas dispersion tube for anhydrous HBr addition, an outlet to a caustic scrubber, a temperature probe, and magnetic stirring. The flask was charged with dry tetraethylammonium bromide (10.81 g), dry CH$_2$Cl$_2$ (450 ml), and 2-butyn-1,4-diol (119.39 g). HBr was fed for 8 h from a cylinder, and the insoluble flakes of 2-butyn-1,4-diol gradually disappeared as the CH$_2$Cl$_2$ solution darkened to a brown opaque color. The HBr feed was discontinued and the apparatus was flushed with N$_2$. The CH$_2$Cl$_2$ was stripped leaving 305 g of a brown liquid that was analyzed by $^1$H-NMR and GC-MS. By GCMS, the product consisted of 84% 2,4-dibromo-2-buten-1-ol, 9% 1,2,4-tribromo-1-butene, and other trace byproducts. The mixture was used as is for the synthesis of 2-bromo-2-butene-1,4-diol.

Example 28

An exemplary non-limiting synthesis of 2-bromo-2-butene-1,4-diol is set forth herein.

A two-liter four-neck flask was set up with a temperature probe, reflux condenser, and mechanical stirring. To the flask was added K$_2$CO$_3$ (500 g) dissolved in deionized water (600 g). Mechanical stirring was set to 200 rpm, and the flask was warmed to 60° C. A crude mixture of 2,4-dibromo-2-buten-1-ol and 1,2,4-tribromo-2-propene (636.0 g) was added. After 24 h the reaction was determined to be complete by NMR analysis (disappearance of the starting material olefinic proton resonance at 6.37 and appearance of the product olefinic proton resonance at 6.27 ppm; in CDCl$_3$). By GC analysis, the product is a mixture of 2-bromo-2-buten-1-ol and oligomers. The aqueous phase was separated (1120 g) and the residue (a reddish colored liquid contaminated with salts) was extracted with CH$_2$Cl$_2$ (300 ml), and vacuum filtered on a sintered frit. The filtrate was condensed via rotary evaporation to yield 360 g (78% yield) of a red oil consisting of 2-bromo-2-butene-1,4-diol and oligomers. The crude product was used as is in formulations testing.

Example 29

Figure 5:
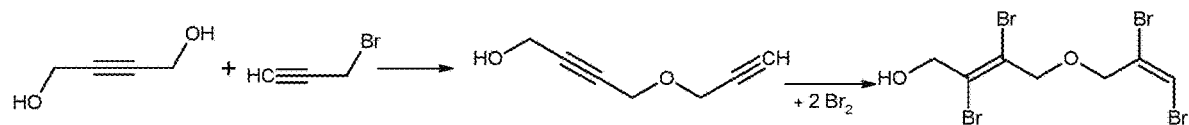
FIG. 5 illustrates a method of preparing a brominated alkenol in accordance with an exemplary embodiment of the disclosure.

An exemplary non-limiting synthesis of the tetrabromo compound shown in FIG. 5 is set forth herein.

(2,3-dibromo-4-(2,3-dibromoprop-2-enyloxy)-2-butyn-1-ol) can be synthesized according to the FIG. 1. Alkylation of 2-butyne-1,4-diol with propargyl bromide can be conducted in the presence of base to give the dialkynyl ether. The dialkynyl ether can be converted to the tetra bromo dialkenyl alcohol by a bromination reaction analogous to Examples 22-24 to give the compound.

EMBODIMENTS

Additionally or alternately, the disclosure can include one or more of the following embodiments.

Embodiment 1. A polyurethane comprising a compound of Formula I or II, where the compound is chemically bonded in the polyurethane through at least one hydroxyl group on the compound.

Embodiment 2. A polyurethane formed from ingredients comprising a compound of Formula I or II, and further comprising at least one polyol and at least one isocyanate or polyisocyanate.

Embodiment 3. A formulation comprising a compound of Formula I or Formula II, at least one polyol, and optionally at least one blowing agent. Also, a polyurethane formed from components comprising a least one isocyanate and/or polyisocyanate and a formulation of a compound of Formula I or Formula II, at least one polyol, and optionally at least one blowing agent.

Embodiment 4. A process for forming a polyurethane, the process comprising contacting at least one isocyanate and/or polyisocyanate and a formulation comprising a compound of Formula I or II and at least one polyol; and allowing the mixture to cure to form the polyurethane.

Embodiment 5. A polyurethane, formulation, or process of one of the previous embodiments, wherein the compound of Formula I is

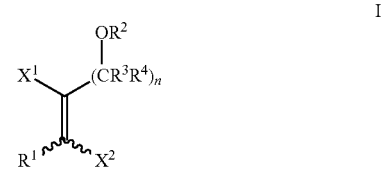

I wherein X$^1$ and X$^2$ are each independently H, Cl, or Br, and at least one of X$^1$ or X$^2$ is Br; R$^1$ is H, Cl, Br, C$_1$-C$_4$ alkyl, or —(CR$^5$R$^6$)$_m$—OR$^7$; R$^2$ is H or C$_2$-C$_8$ alkylhydroxyl; R$^3$, R$^4$, R$^5$ and R$^6$ are each independently H, C$_1$-C$_8$ alkyl, C$_2$-C$_8$ alkenyl, C$_1$-C$_8$ haloalkyl or C$_2$-C$_8$ haloalkenyl; R$^7$ is H, C$_1$-C$_8$ alkyl, C$_2$-C$_8$ alkenyl, C$_1$-C$_8$ haloalkyl, C$_2$-C$_8$ haloalkenyl or C$_2$-C$_8$ alkylhydroxyl; n=1-4; and m=1-4.

Embodiment 6. A polyurethane, formulation, or process of one of the previous embodiments, wherein the compound of Formula I is

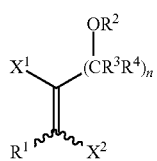

wherein $X^1$ and $X^2$ are each independently H, Cl, or Br, and at least one of $X^1$ or $X^2$ is Br; $R^1$ is H, Cl, Br, $C_1$-$C_4$ alkyl, or —$(CR^5R^6)_m$—$OR^7$; $R^2$ is H or $C_2$-$C_8$ alkylhydroxyl; $R^3$, $R^4$, $R^5$ and $R^6$ are each independently H, $C_1$-$C_8$ alkyl, $C_2$-$C_8$ alkenyl, or $C_2$-$C_8$ haloalkenyl; $R^7$ is H, $C_1$-$C_4$ alkyl, $C_2$-$C_8$ haloalkenyl or $C_2$-$C_8$ alkylhydroxyl; n=1-4; and m=1-4.

Embodiment 7. A polyurethane, formulation, or process of one of the previous embodiments, wherein the compound of Formula I is

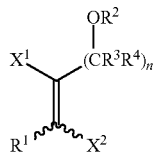

wherein $X^1$ and $X^2$ are each independently H, Cl, or Br, and at least one of $X^1$ or $X^2$ is Br; $R^1$ is H, Cl, Br, $C_1$-$C_4$ alkyl, or —$(CR^5R^6)_m$—$OR^7$; $R^2$ is H or $C_2$-$C_4$ alkylhydroxyl; $R^3$, $R^4$, $R^5$ and $R^6$ are each independently H, $C_1$-$C_4$ alkyl, $C_2$-$C_4$ alkenyl, or $C_2$-$C_4$ haloalkenyl; $R^7$ is H, $C_1$-$C_4$ alkyl, $C_2$-$C_4$ haloalkenyl or $C_2$-$C_4$ alkylhydroxyl; n=1-4; and m=1-4.

Embodiment 8. A polyurethane, formulation, or process of one of the previous embodiments, wherein the compound of Formula II can be described as

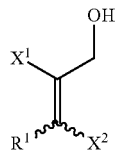

wherein, $X^1$ and $X^2$ are each independently H, Cl, or Br, and at least one of $X^1$ or $X^2$ is Br; $R^1$ is H, Cl, Br, $C_1$-$C_4$ alkyl, or —$(CR^5R^6)_m$—$OR^7$; $R^5$ and $R^6$ are each independently H, $C_1$-$C_4$ alkyl, $C_2$-$C_4$ alkenyl, $C_1$-$C_4$ haloalkyl or $C_2$-$C_4$ haloalkenyl; $R^7$ is H, $C_1$-$C_4$ alkyl, $C_2$-$C_4$ alkenyl, $C_1$-$C_4$ haloalkyl, $C_2$-$C_4$ haloalkenyl or $C_2$-$C_4$ alkylhydroxyl; and m=1-4.

Embodiment 9. A polyurethane, formulation, or process of one of the previous embodiments, wherein $R^2$ is H, more preferably where $R^2$ is H, n=1, and $R^3$ and $R^4$ are H.

Embodiment 10. A polyurethane, formulation, or process of one of the previous embodiments, wherein $R^1$ is H, Br or —$(CR^5R^6)_m$—$OR^7$. $R^1$ can preferably be H or Br. $R^1$ can also preferably be —$(CR^5R^6)_m$—$OR^7$, where $R^5$ and $R^6$ are H and m=1.

Embodiment 11. A polyurethane, formulation, or process of one of the previous embodiments, wherein the $R^1$ is H or Br, and $R^2$ is $C_2$ to $C_8$ alkylhydroxyl, preferably a $C_2$ to $C_4$ alkylhydroxyl.

Embodiment 12. A polyurethane, formulation, or process of one of the previous embodiments, wherein $R^2$ is H, $R^1$ is —$(CR^5R^6)_m$—$OR^7$, and $R^7$ is $C_1$-$C_4$ alkyl.

Embodiment 13. A polyurethane, formulation, or process of one of the previous embodiments, wherein n is 2-4, and $R^2$ is H.

Embodiment 14. A polyurethane, formulation, or process of one of the previous embodiments, wherein $X^1$ and $X^2$ are both Br.

Embodiment 15. A polyurethane, formulation, or process of one of the previous embodiments, wherein $X^1$ is Br and $X^2$ is Cl or H.

Embodiment 16. A polyurethane, formulation, or process of one of the previous embodiments, wherein $X^1$, $X^2$ and $R^1$ are each Br. Alternatively, $X^1$ is Br, $X^2$ is H, and $R^1$ is H.

Embodiment 17. A polyurethane, formulation, or process of one of the previous embodiments, wherein $R^1$ is H, and when one of $X^1$ and $X^2$ is Br, then the other is Cl. Alternatively, $R^1$ is H, and when one of $X^1$ and $X^2$ is Br, then the other is H.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based can be readily utilized as a basis for the design of other structures, methods, and systems for carrying out the several purposes of the embodiments and claims presented in this application. It is important, therefore, that the claims be regarded as including such equivalent constructions.

We claim:

1. A polyurethane prepared by reacting at least one isocyanate and/or polyisocyanate and a compound of Formula 1,

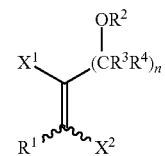

wherein
$X^1$ and $X^2$ are each independently H, Cl, or Br, and at least one of $X^1$ or $X^2$ is Br;
$R^1$ is H, Cl, Br, $C_1$-$C_4$ alkyl, or —$(CR^5R^6)_m$—$OR^7$;
$R^2$ is a $C_2$-$C_8$ alkylhydroxyl;
$R^3$, $R^4$, $R^5$ and $R^6$ are each independently H, $C_1$-$C_8$ alkyl, $C_2$-$C_8$ alkenyl, $C_1$-$C_8$ haloalkyl or $C_2$-$C_8$ haloalkenyl;
$R^7$ is H, $C_1$-$C_8$ alkyl, $C_2$-$C_8$ alkenyl, $C_1$-$C_8$ haloalkyl, or $C_{2-8}$ haloalkenyl;
n=1-4;
m=1-4; and the compound of Formula 1 is chemically bonded in the polyurethane foam through at least one hydroxyl group on the compound.

2. The polyurethane of claim 1, wherein $R^1$ is H.

3. The polyurethane of claim 1, wherein n is 1 and m, when present, is 1.

4. The polyurethane of claim 1, wherein $X^1$ is Br and $X^2$ is Cl or H.

5. The polyurethane of claim 1, wherein $X^1$ is Br, $X^2$ is H, and $R^1$ is H.

6. The polyurethane of claim 1, wherein $X^1$, $X^2$ and $R^1$ are each Br.

7. The polyurethane of claim 1, wherein n is 2-4.

8. The polyurethane of claim 1, wherein $R^1$ is H, and one of $X^1$ and $X^2$ is Br, while the other is Cl.

9. The polyurethane of claim 1, wherein one of $X^1$ and $X^2$ is Br, while the other is H.

10. The polyurethane of claim 1, wherein the compound of Formula 1 is:

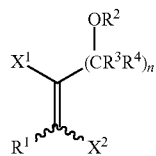

11. A formulation comprising a compound of Formula I and at least one polyol,

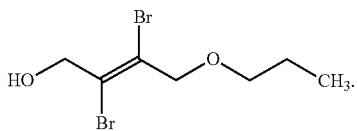

wherein $X^1$ and $X^2$ are each independently H, Cl, or Br, and at least one of $X^1$ or $X^2$ is Br;

$R^1$ is H, Cl, Br, $C_1$-$C_4$ alkyl, or —$(CR^5R^6)_m$—$OR^7$;

$R^2$ is a $C_2$ to $C_8$ alkylhydroxyl;

$R^3$, $R^4$, $R^5$ and $R^6$ are each independently H, $C_1$-$C_8$alkyl, $C_2$-$C_8$ alkenyl, $C_1$-$C_8$ haloalkyl or $C_2$-$C_8$ haloalkenyl;

$R^7$ is H, $C_1$-$C_8$alkyl, $C_2$-$C_8$ alkenyl, $C_1$-$C_8$ haloalkyl, or $C_{2-8}$ haloalkenyl;

n=1-4; and m=1-4.

12. The formulation of claim 11, wherein $R^1$ is H.

13. The formulation of claim 11, wherein n is 1 and m, when present, is 1.

14. The formulation of claim 11, wherein $X^1$ is Br and $X^2$ is Cl or H.

15. The formulation of claim 11, wherein $X^1$ is Br, $X^2$ is H, and $R^1$ is H.

16. The formulation of claim 11, wherein $X^1$, $X^2$ and $R^1$ are each Br.

17. The formulation of claim 11, wherein the compound of Formula 1 is:

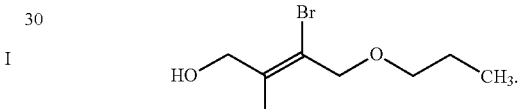

18. The formulation of claim 11, further comprising a blowing agent.

* * * * *